United States Patent [19]
Izatt et al.

[11] Patent Number: 6,006,128
[45] Date of Patent: Dec. 21, 1999

[54] DOPPLER FLOW IMAGING USING OPTICAL COHERENCE TOMOGRAPHY

[76] Inventors: Joseph A. Izatt; Manish D. Kulkarni; Siavash Yazdanfar; Andrew Rollins; Michael V. Sivak, all of c/o University Hospitals of Cleveland Department of Medicine Division of Gastroenterology 11100 Euclid Ave., Cleveland, Ohio 44106-5066

[21] Appl. No.: 09/088,562

[22] Filed: Jun. 2, 1998

Related U.S. Application Data

[60] Provisional application No. 60/047,358, Jun. 2, 1997.

[51] Int. Cl.[6] ................................................ A61B 5/02
[52] U.S. Cl. ............................................................ 600/476
[58] Field of Search ...................... 600/473, 476, 600/479, 480, 477, 475, 309, 310, 407; 356/39, 345, 346; 250/356.1, 363.01, 370.08

[56] References Cited

U.S. PATENT DOCUMENTS

| | | | |
|---|---|---|---|
| 4,063,549 | 12/1977 | Beretsky et al. | 128/2 |
| 5,158,090 | 10/1992 | Waldman et al. | 128/664 |
| 5,200,819 | 4/1993 | Nudelman et al. | 358/98 |
| 5,353,802 | 10/1994 | Ollmar | 128/734 |
| 5,459,570 | 10/1995 | Swanson et al. | 356/345 |
| 5,491,524 | 2/1996 | Hellmuth et al. | 351/212 |
| 5,493,109 | 2/1996 | Wei et al. | 250/201.3 |
| 5,501,226 | 3/1996 | Petersen et al. | 128/691 |
| 5,549,114 | 8/1996 | Petersen et al. | 128/691 |
| 5,565,986 | 10/1996 | Knüttel | 356/346 |
| 5,644,642 | 7/1997 | Kirschbaum | 382/103 |

OTHER PUBLICATIONS

Optical Coherence–Domain Reflectometry: A New Optical Evaluation Technique, R.C. Youngquist et al., *Optics Letters*, vol. 12, No. 3, pp. 158–160 (Mar. 1997).

Optical Coherence Tomography, D. Huang et al., *Science*, vol. 254, pp. 1178–1181 (Nov. 22, 1991).

Systems and Transforms with Applications in Optics, A. Papoulis, pp. 254–293, McGraw–Hill Book Company (1968).

Maximum–Likelihood Deconvolution, A Journey into Model–Based Signal Processing, J.M. Mendel, pp. 1–77, Springer–Verlag New York Inc. (1990).

(List continued on next page.)

*Primary Examiner*—Scott M. Getzow
*Attorney, Agent, or Firm*—Thompson Hine & Flory LLP

[57] ABSTRACT

A method for generating a velocity-indicating, tomographic image of a sample in an optical coherence tomography system includes the steps of (a) acquiring cross-correlation data from the interferometer; (b) generating a grayscale image from the cross-correlation data indicative of a depth-dependent positions of scatterers in the sample; (c) processing the cross-correlation data to produce a velocity value and location of a moving scatterer in the sample; (d) assigning a color to the velocity value; and (f) merging the color into the grayscale image, at a point in the grayscale image indicative of the moving scatterer's location, to produce a velocity-indicating, tomographic image. Preferably a first color is assigned for a positive velocity value and a second color is assigned for a negative velocity value.

21 Claims, 13 Drawing Sheets

OTHER PUBLICATIONS

Micron–Resolution Biomedical Imaging With Optical Coherence Tomography, J. Izatt et al., *Optics & Photonics News* (Oct. 1993).

Characterization of fluid flow velocity by optical Doppler tomography, X. Wang et al., *Optics Letters,* vol. 20, No. 11 (Jun. 1, 1995).

Optical Doppler tomography imaging of fluid flow velocity in highly scattered media, Z. Chen et al., *Optics Letters,* vol. 22, No. 1, pp. 64–66 (Jan. 1, 1997).

Distributed laser Doppler velocimeter, V. Gusmeroli et al., *Optics Letters,* vol. 16, No. 17 (Sep. 1, 1991).

Noninvasive imaging of in vivo blood flow velocity using optical Doppler tomography, Z. Chen et al., *Optics Letters,* vol. 22, No. 14 (Jul. 15, 1997).

Cleo '97: Summaries of papers presented at the Conference on Lasers and Electro–Optics, 1997 OSA Technical Digest Series, vol. 11, Conference Edition, pp. 211–212, Baltimore, MD (May, 18–23, 1997).

Real–time Two Dimensional Blood Flow Imaging Using an Autocorrelation Technique, C. Kasai et al., *IEEE Transactions on Sonics and Ultrasonics,* vol. SU–32, No. 3 (May 1985).

*Doppler Ultrasound: Physics, Instrumentation, and Clinical Applications,* Chapter 6: Basic Doppler Electronics and Signal Processing, D.H. Evans et al., pp. 84–107, John Wiley & Sons, New York (1989).

*Vascular Diagnosis, 4th Ed.,* Chapter 12: Principles and pitfalls of real–time color flow imaging, F.W. Kremkau, pp. 90–105, Mosby Year–Book, Inc. Missouri (1993).

*Vascular Diagnosis, 4th Ed.,* Chapter 11: Pulsed Doppler ultrasound for blood velocity measurements, K.W. Beach et al., pp. 83–89, Mosby Year–Book, Inc., Missouri (1993).

Velocity–estimation accuracy and frame–rate limitations in color Doppler optical coherence tomography, M.D. Kulkarni et al., *Optics Letters,* vol. 23, No. 13 (Jul. 1, 1998).

Investigating laser–blood vessel interaction with color Doppler optical coherence tomography, J.K. Barton et al., *Progress in Biomedical Optics: Proceedings of Coherence Domain Optical Methods in Biomedical Science and Clinical Applications II,* San Jose CA, *SPIE,* vol. 3251 (Jan. 27–28, 1998).

Diagnostic blood flow monitoring during therapeutic interventions using color Doppler optical coherence tomography, S. Yazdanfar et al., *Progress in Biomedical Optics: Proceedings of Coherence Domain Optical Methods in Biomedical Science and Clinical Applications II,* San Jose, CA, *SPIE,* vol. 3251 (Jan. 27–28, 1998).

High Resolution imaging of in vivo cardiac dynamics using color Doppler optical coherence tomography, S. Yazdanfar et al., *Optics Express,* vol. 1, No. 13 (Dec. 22, 1997).

In vivo bidirectional color Doppler flow imaging of picoliter blood volumes using optical coherence tomography, J.A. Izatt et al., *Optics Letters,* vol. 22, No. 18 (Sep. 15, 1997).

In vivo Doppler flow imaging of picoliter blood volumes using optical coherence tomography, J.A. Izatt et al., Cleo '97: Summaries of papers presented at the Conference on Lasers and Electro–Optics, *1997 OSA Technical Digest Series,* vol.11, Conference Edition, Baltimore, MD (May 18–23, 1997).

Optical Coherence Tomography for Biodiagnostics, J.A. Izatt et al., *Optics & Photonicvs News* (May 1997).

Doppler Flow Imaging Using Optical Coherence Tomography, J.A. Izatt et al., Cleo '96 Postdeadline Papers, Conference on Lasers and Electro–Optics, Anaheim, CA (Jun. 02–07, 1996).

Model for laser Doppler measurements of blood flow in tissue, R. Bonner et al., *Applied Optics,* vol. 20, No. 12 (Jun. 15, 1981).

DOPPLER FLOW IMAGING USING OPTICAL COHERENCE TOMOGRAPHY

CROSS-REFERENCE TO RELATED APPLICATIONS

This application claims priority under 35. U.S.C. §119 from Provisional Application Ser. No. 60/047,358 filed Jun. 2, 1997, the entire disclosure of which is incorporated herein by reference.

BACKGROUND

Optical coherence tomography (OCT) is a technology that allows for non-invasive, cross-sectional optical imaging of biological media with high spatial resolution and high sensitivity. OCT is an extension of low-coherence or white-light interferometry, in which a low temporal coherence light source is utilized to obtain precise localization of reflections internal to a probed structure along an optic axis. In OCT, this technique is extended to enable scanning of the probe beam in the direction perpendicular to the optic axis, building up a two-dimensional reflectivity data set, used to create a cross-sectional gray-scale or false-color image of internal tissue backscatter.

OCT has been applied to imaging of biological tissue in vitro and in vivo, although the primary applications of OCT developed to date have been for high resolution imaging of transparent tissues, such as ocular tissues. U.S. patent application Ser. No. 09/040,128, filed Mar. 17, 1998, provides a system and method for substantially increasing the resolution of OCT and also for increasing the information content of OCT images through coherent signal processing of the OCT interferogram data. This system is capable of providing cellular resolution (i.e., in the order of 5 micrometers). Accordingly, OCT can be adapted for high fidelity diagnosis of pre-cancerous lesions, cancer, and other diseases of the skin, bladder, lung, GI tract and reproductive tract using non-invasive medical diagnostics.

In such diagnostic procedures utilizing OCT, it would also be desirable to monitor the flow of blood and/or other fluids, for example, to detect peripheral blood perfusion, to measure patency in small vessels, and to evaluate tissue necrosis. Another significant application would be in retinal perfusion analysis. Monitoring blood-flow in the retina and choroid may have significant applications in diagnosis and monitoring macular degeneration and other retinal diseases. Accordingly, it would be advantageous to combine Doppler flow monitoring with the above micron-scale resolution OCT imaging in tissue.

Wang, et al., "Characterization of Fluid Flow Velocity by Optical Doppler Tomography," *Optics Letters*, Vol. 20, No. 11, Jun. 1, 1995, describes an Optical Doppler Tomography system and method which uses optical low coherence reflectrometry in combination with the Doppler effect to measure axial profiles of fluid flow velocity in a sample. A disadvantage of the Wang system is that it does not provide a method to determine direction of flow within the sample and also does not provide a method for generating a two-dimensional color image of the sample indicating the flow velocity and directions within the image.

U.S. Pat. No. 5,549,114 to Petersen, et al. also provides an optical coherence tomography system capable of measuring the Doppler shift of backscattered light from flowing fluid within a sample. However, similar to Wang, et al., Petersen, et al. does not disclose a system or method for displaying the direction of flow within the sample, nor does Petersen, et al. disclose a system or method for providing a two-dimensional color image of the sample which indicates the velocity and directions of flow of fluids within the sample.

SUMMARY

The present invention involves an advancement in OCT technology that provides for quantitative measurements of flow in scattering media by implementing systems for increased interferogram acquisition accuracy, coherent signal processing and display. The present invention provides a combination of micron-scale resolution tomographic optical imaging of a tissue sample simultaneously with Doppler flow monitoring of blood and other body fluids within the sample volume.

The present invention utilizes an OCT data acquisition system to obtain precise localization of reflections internal to the sample along the optic axis. Scanning the OCT probe beam in a direction perpendicular to the optic axis builds up a two-dimensional data set comprising a gray-scale cross-sectional image of internal tissue backscatter. The data acquisition system may also utilize a calibration interferometer for providing sub-100 nm accuracy calibration of the reference arm position during interferogram acquisition. In combination with the production of the cross-sectional gray-scale image internal tissue backscatter, the present invention also provides a two-dimensional color data image representing the Doppler flow velocity and directions of moving scatterers within the sample. The method for generating the two-dimensional, color, Doppler image is generally as follows:

For each axial reference arm scan ("A-scan"), interferometric data is acquired. This interferometric data corresponds to a cross-correlation measurement of the light returning from the reference arm and the light backscattered from the volume of potentially moving scatterers illuminated by the sample arm probe beam. The acquired interferometric data is first band-pass filtered for noise reduction. Next, the filtered data is coherently demodulated at a frequency corresponding to the Doppler shift induced by the reference mirror of the interferometer to produce an array of in-phase data values vs. time and an array of quadrature data values vs. time. As those of ordinary skill in the art will realize, the time element in these arrays is directly proportional to the reference arm length, and in turn, is directly proportional to the scanning depth into the sample.

Next, a starting time and a time window is selected. The selected starting time corresponds to a starting depth and the selected time window corresponds to a depth-range that is preferably longer than or equal to the coherence length of the light source of the low-coherence interferometer. At the selected starting time, the values of the in-phase array and the quadrature array corresponding to the selected time window are extracted from the in-phase and quadrature arrays and passed into a Fourier transform (FT) circuit or algorithm to obtain a power spectrum (localized Doppler spectrum) for that particular time window (depth range).

From this power spectrum, a central velocity estimate is calculated to obtain an estimate of the mean scatter velocity for that particular time window. In one embodiment, the central velocity estimate is obtained by calculating a centroid for the power spectrum. This velocity estimate will have a sign and a magnitude. Next, one of two colors is assigned for to the velocity estimate, the particular one of two colors assigned being determined according to the sign of the velocity estimate (i.e., blue for positive values and red for negative values). The brightness, intensity or density of the color to assign to the window is determined by the magnitude of the velocity estimate. The resultant color and brightness is applied to an image pixel, or to a plurality of image pixels in a velocity profile (which is an array of image pixels corresponding to the particular A-scan). The particular pixel(s) to which the color and brightness is applied is the pixel(s) corresponding to the particular depth range of the selected window.

Next, at a predetermined point past the starting time, another time window of in-phase and quadrature data is extracted from the in-phase and quadrature arrays. From this next time window, a velocity estimate is calculated as described above, a color is assigned for this velocity estimate, and the color is applied to the velocity profile corresponding to the particular depth range of this next time window. New windows will thereafter be repeatedly extracted and processed to generate a complete velocity profile for the particular A-scan. In one embodiment of the invention, this complete velocity profile is a one-dimensional array of colorized image pixels corresponding to the lateral position of the sample probe.

Preferably, multiple A-scans are performed for a sample, each A-scan corresponding to a particular lateral position of the sample arm with respect to the sample. Alternatively, for angular scanning implementations of OCT, subsequent A-scans are arranged into a radial array. It is to be understood that while the present invention describes multiple A-scans as being displaced laterally, it is within the scope of the invention to utilize the same signal processing algorithms described herein with respect to these acquisition and display methods. The above process of generating a velocity profile is performed for each A-scan taken. The processing can be performed either in real-time or after all of the A-scans have been taken and stored in memory. Thereafter, the velocity profiles are aligned side-by-side to create a two-dimensional colorized Doppler image indicating the direction and velocity of moving scatterers within the sample. This two-dimensional colorized Doppler image may then be merged with, or superimposed onto the gray-scale tissue backscatter image to create a complete image of the sample showing internal tissue scatterers as well as the velocity and direction of moving scatterers within the sample.

The time windows extracted from the real array and imaginary arrays, described above, can be either non-overlapping (adjacent) or overlapping time windows. If non-overlapping windows are used, the color determined by the above process would be applied to the entire time window (i.e., if the time windows correspond to a sample depth that will be approximately 10 pixels deep in the final image, the color determined by the above process would be applied to all 10 pixels in the colorized Doppler image). But if overlapping time windows are used, the velocity value determined by the above process can be applied to a time (depth) range equal to the amount that the time windows do not overlap. For example, if the windows overlap entirely except for a sample depth corresponding to a depth of approximately one pixel in the final image, the color determined by the above process would be applied to only a single pixel in the colorized Doppler image. Thus, while more processing would be required to process the entire A-scan data, the overlapping time windows would provide a much more precise Doppler image than the non-overlapped time windows.

An alternate scheme for color coding the velocity information assigns a specific color or shade to each velocity and encodes into brightness, the magnitude of the signal or equivalently, the reflectivity of the tissue at the site. This alternate color coding scheme may offer some advantages in image rendering speed and ease of interpretation. In this scheme, a blood vessel would appear as a series of concentric rings, whose radius is smallest at the vessel's center.

Prior to merging the two-dimensional colorized Doppler image with the gray-scale image the user may be prompted to select both positive and negative, minimum threshold and maximum saturation velocities. These threshold and saturation velocities are then applied to the velocity array or to the velocity profile to provide an upper and lower bound to the velocity display color scale which allows all desired velocities to be displayed. Velocities which are larger than the maximum positive and negative saturation velocities, respectively, may be rendered the same color (brightness, shade, etc.) as the positive or negative maximum saturation velocities themselves, or else may be rendered in some other distinctive color (brightness, shade, ect.) in order to indicate that the velocity color scale was saturated at that location. Velocities which are smaller than the positive and negative threshold velocities are rendered as transparent to indicate that flow was not detected in that image region, and to allow for visualization of the underlying gray-scale magnitude reflectivity image.

It has been shown, mathematically, that a better velocity estimate can be obtained for a particular position within the sample (i.e., within a particular time window and lateral position) by taking multiple A-scans for that lateral position and then averaging the velocity estimates together. Accordingly, in one embodiment of the invention, multiple A-scans are taken for each lateral position of the sample arm, and the velocity estimates calculated for each A-scan taken are averaged together to produce a more accurate velocity estimate for that particular lateral position of the sample arm. Alternatively, better velocity estimates may also be obtained by averaging estimated windowed spectra obtained from multiple A-scans for each time window and lateral position, followed by calculating the centroids of the averaged spectra.

It is also known that the spatial resolution of the velocity estimate is limited by the window size, the larger the window—the lower the spatial resolution. But velocity resolution is inversely related to the window size, the larger the window—the better the velocity resolution. Two alternate embodiments of the invention, however, overcome this trade-off and provide for simultaneous high spatial resolution and high velocity resolution. This is done, in a general sense, by slowing down the time for taking the A-scan.

In a first alternate embodiment, for each position of the reference arm, instead of one set of in-phase and quadrature data taken, multiple sets of in-phase and quadrature data are taken. Thus, instead of calculating a velocity estimate for a window pertaining to multiple positions of the reference arm, the velocity estimate is calculated for a block of data pertaining substantially to a single position (depth) of the reference arm. With this alternate embodiment, it is not necessary to take the multiple sets of data at a single position of the reference arm, so long as all the readings are taken within a range of reference arm movement less than the coherence length of the interferometer's light source.

In a second alternate embodiment, instead of one A-scan being taken for each lateral position of the sample arm, multiple A-scans are taken at each lateral position of the sample arm. The in-phase and quadrature data are then arranged into a two-dimensional matrix by aligning the one-dimensional (vertical) matrices for each A-scan taken side-by-side. Thus, instead of calculating a velocity estimate for a window pertaining to multiple positions of the reference arm (a vertical "column" window), the velocity estimate is calculated for a single position (a horizontal "row" window) of the reference arm. The step of taking multiple A-scans for each lateral position of the sample arm may be accomplished by: (a) incrementally advancing the sample arm laterally and taking the multiple A-scans for each incremental advance of the sample arm; (b) laterally sweeping the sample arm over the sample a multitude of times, taking one A-scan for each lateral position of the sample arm; or (c) some combination of (a) and (b).

The above steps for converting the interferogram data into power spectrum data may be performed by a bank of narrow-band band-pass filters (NBPF), where each NBPF passes a particular frequency along the power spectrum frequency scale. The outputs of each NBPF may be input directly into the centroid calculation. This method eliminates the need for the short-time Fourier transform circuit/algorithm and, may also eliminate the need for the coherent demodulation circuit/algorithm. Thus, this method provides faster and cheaper signal processing.

The above steps for converting the interferogram data into power spectrum data may also be performed by a bank of coherent demodulators and a corresponding bank of low-pass filters, where each demodulator demodulates the data at a particular frequency along the power spectrum frequency scale. This approach offers several advantages for the acquisition of local spectral information. First, the output of each of the detection channels is nearly instantaneous, allowing for substantially real-time implementation of CDOCT. Further, the electronic components are readily available.

This latter approach may also be accomplished using a synthesized multi-frequency demodulating waveform, a mixer, and a low-pass filter. In this form, a reference waveform is synthesized as a sum of a desired number of sinusoids at a range of frequencies. These frequencies are mixed in a single mixer with the interferogram data, and the resulting mixed signal is then low-pass filtered. While this alternate embodiment represents a substantial savings in the number of components required, it does not provide estimation of the complete frequency spectrum within the analysis region.

Finally, the present invention provides two implementations of scatterer velocity estimation and one implementation of turbulence estimation using an auto-correlation method, which is based on a mathematical derivation that estimates the central velocity and turbulence of the fluid flow in the sample as being related to the first and second moments of the Doppler-shifted frequency power spectrum. The first utilizes a complex demodulated detector output to obtain both the centroid velocity and an estimate of the power spectrum variance. The second is a much simpler version and provides an estimate of the central velocity only.

Accordingly, it is an object of the present invention to provide a method for generating a two- or three-dimensional color image of a sample indicating the flow velocity and directions within the image using an OCT acquisition system.

It is a further object of the present invention to provide a method for generating a velocity-indicating, tomographic image of a sample in an optical coherence tomography system including the steps of (a) acquiring cross-correlation data from the interferometer; (b) generating a grayscale image from the cross-correlation data indicative of a depth-dependent positions of scatterers in the sample; (c) processing the cross-correlation data to produce a velocity value and location of a moving scatterer in the sample; (d) assigning a color to the velocity value; and (f) merging the color into the grayscale image, at a point in the grayscale image indicative of the moving scatterer's location, to produce a velocity-indicating, tomographic image.

These and other objects and advantages of the present invention will be apparent from the following description, the appended claims and the attached drawings.

DETAILED DESCRIPTION

Figure 1:
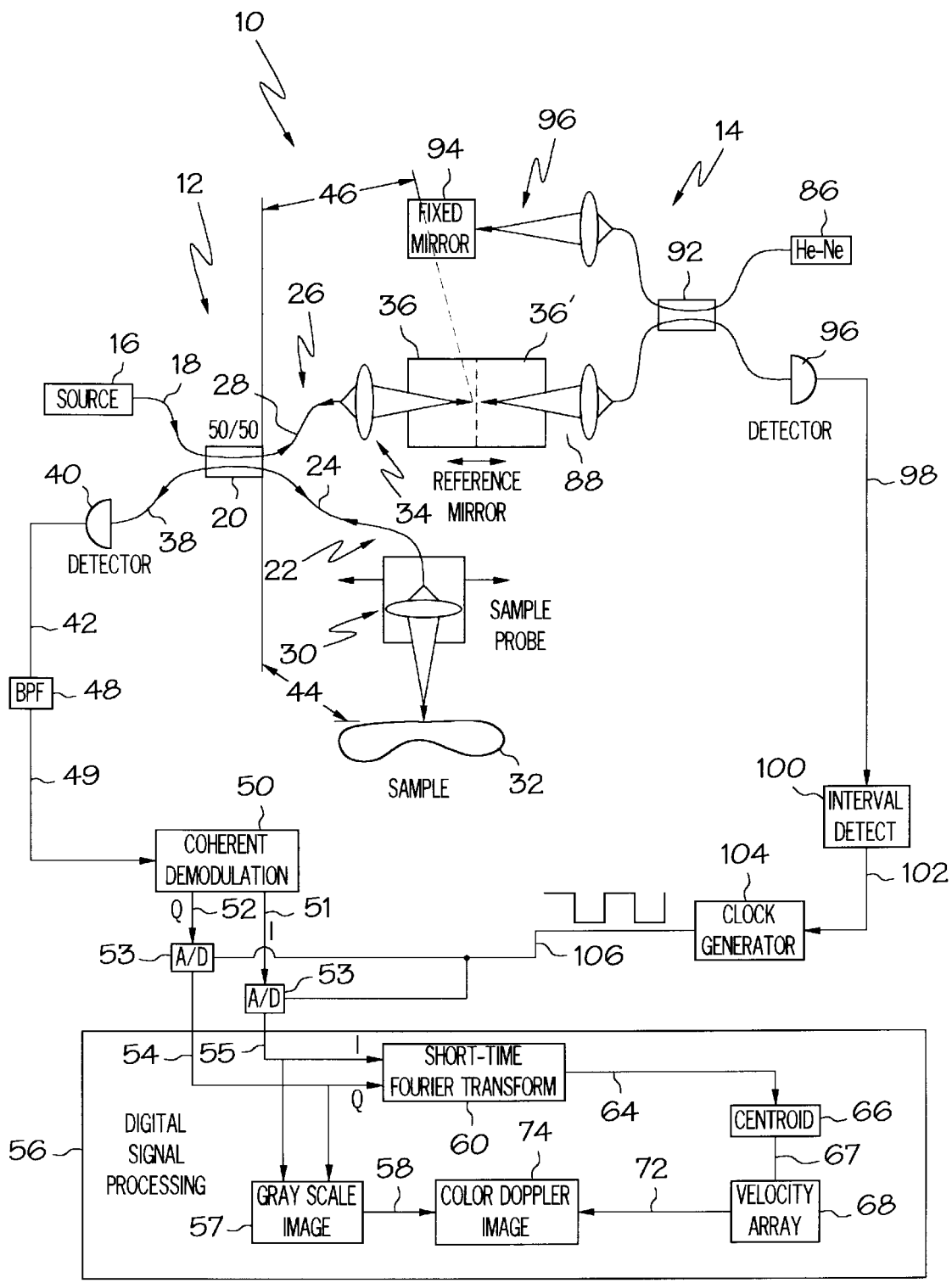
FIG. 1 is a schematic, block diagram representation of an OCT data acquisition and digital signal processing system of the present invention.

As shown in FIG. 1, an OCT data acquisition system 10 for use with the present invention includes a low-coherence interferometer 12 and, optionally, a high-coherence calibration interferometer 14. The low-coherence interferometer 12 includes a light source, such as a super-luminescent diode ("SLD") source 16, a fiber-optic source line 18 coupled between the SLD 16 and a fiber-optic beam splitter (such as a 50/50 fiber coupler) 20. Other known suitable light sources include a semiconductor optical amplifier ("SOA"), which is a higher-powered light source for high-speed OCT, or a rare-earth doped fiber amplifier commonly used in optical communication. The beam splitter 20 separates the light received from the source line 18 into two beams; one transmitted to a sample arm 22 via an optical fiber 24, and the other to a reference arm 26 via an optical fiber 28. The sample arm optical fiber 24 is coupled to a sample probe 30 adapted to focus light to a sample 32 and to receive the light reflected back from the sample 32. The reflected light received back from the sample is transmitted back to the beam splitter 20 via the sample arm optical fiber 24. Preferably, the sample probe 30 has an adjustable focal length, thus allowing adjustment of the focal spot size, working distance and depth of focus.

The fiber 28 is coupled to a reference probe 34 adapted to focus light received from the reference arm optical fiber 28 to a translating reference mirror 36 (usually mounted on a galvanometer), and to receive the light reflected back from the reference mirror 36. The reflected light received back from the reference mirror 36 is transmitted back to the beam splitter 20 via the reference arm optical fiber 28. The reflected light received by the beam splitter 20, back from both the sample arm optical fiber 24 and the reference arm optical fiber 28 is combined and transmitted on the fiber-optic line 38 to a photodetector 40. The photodetector produces an analog signal 42, responsive to the intensity of the incident electric field. An example of a photodetector for use with the present invention is Model 1811, commercially available from New Focus, Inc., Mountain View, Calif.

The optical path length 44 of the sample arm 22 is a function of the distribution of scattering sites within the sample 32, while the optical path length 46 of the reference arm 26 changes with the translation of the reference mirror 36. Because a low coherence light source is used, a fringe pattern (interferometric signal) is produced at the photodetector 40 when the optical path length 44 to a reflecting or scattering site within the sample 32 matches the optical path length 46 of the reference arm 26, within a coherence length. The fringe pattern observed is a function of the optical path length distance between the sample and reference arms. Translating the reference mirror 36 provides interferogram data, which is the optical path length dependent cross-correlation function of the light retro-reflected from the reference mirror 36 and the sample 32. Collecting interferogram data for a point on the sample for one reference mirror cycle is referred to as collecting an "A-scan." The A-scan data provides a one-dimensional profile of reflecting and scattering sites of the sample 32 vs. depth within the sample.

It will be apparent to one of ordinary skill in the art that there are many known methods and/or mechanisms for injecting the above reference arm delay, other than a translating reference mirror; all of which are within the scope of the present invention. Alternative reference arm optical delay strategies include those which modulate the length of the reference arm optical fiber by using a piezo-electric fiber stretcher, methods based on varying the path length of the reference arm light by passing the light through rapidly rotating cubes or other rotating optical elements, and methods based on Fourier-domain pulse-shaping technology which modulate the group delay of the reference arm light by using an angularly scanning mirror to impose a frequency-dependent phase on the reference arm light after having been spectrally dispersed. This latter technique, which is the first to have been shown capable of modulating the reference arm light fast enough to acquire OCT images at video rate, depends upon the fact that the inverse Fourier transform of a phase ramp in the frequency domain is equal to a group delay in the time domain. This latter delay line is also highly dispersive, in that it can impose different phase and group delays upon the reference arm light. For such a dispersive delay line, the OCT interferogram fringe spacing depends upon the reference arm phase delay, while the position of the interferogram envelope at any time depends upon the reference arm group delay. All types of delay lines can be described as imposing a Doppler shift frequency $f_r$ on the reference arm light, where Doppler shift frequency in this context is defined as the time derivative of the phase of the central frequency component present in the interferometric signal. For the purposes of this disclosure, this definition of Doppler shift frequency encompasses all possible reference arm delay technologies.

An analog band-pass filter 48 filters the analog interferogram data signal 42 to reduce excess noise. The filtered analog interferogram data 49 is sent to an analog demodulator 50, which coherently demodulates the interferogram data at the frequency corresponding to the Doppler shift induced by the reference mirror to produce a series 52 of analog in-phase "I" component data vs. time and a series 51 of analog quadrature "Q" component data vs. time. The analog in-phase "I" data series 52 and analog quadrature "Q" data series 51 are fed into analog-to-digital ("A/D") converters 53, which convert the analog in-phase "I" data series 52 and analog quadrature "Q" data series 51 into a digital in-phase data array 55 and a digital quadrature data array 54, respectively. These digital data arrays 54, 55 are then sent to the digital signal processing circuitry/system ("DSP") denoted by block 56. It is within the scope of the invention that the above analog-to-digital conversion can be performed prior to, or in-between the band-pass filtering and demodulating steps, and it is also within the scope of the invention that the band-pass filtering and coherent demodulation steps can be performed by the digital signal processing circuitry 56. But utilizing the analog band-pass filter 48 and the analog coherent demodulator 50 substantially increases processing speed and reduces system cost.

The series 51 of analog quadrature data and the series 52 of analog in-phase data comprise the complex demodulated interferogram data. The in-phase series 52 represents the values of the real component of the interferogram data and the quadrature series 51 represents the values of the imaginary component of the interferogram data.

As indicated in block 57 the in-phase and quadrature arrays of interferogram data are processed by the DSP 56 to generate a one-dimensional reflectivity profile 58 of internal backscatter locations vs. depth. Suitable systems and methods for generating a gray-scale or false-color image of internal backscatter locations vs. depth are described in U.S. patent application Ser. No. 09/040,128, filed Mar. 17, 1998, the disclosure of which is incorporated herein by reference. Additionally, it is within the scope of the invention that the gray-scale image may be generated according to other conventional incoherent envelope detection methods, as will be apparent to those of ordinary skill in the art.

The OCT Doppler flow monitoring of the present invention is based on the principle that Doppler shifts in light backscattered from moving objects in the sample 32 (e.g., flowing erythrocytes in blood vessels) either add to or subtract from the fixed Doppler shift frequency $f_r$ induced by the reference arm delay (for the case of the translating reference arm mirror 36, Doppler shift frequency $f_r=2V_r/\lambda$, where $V_r$ is the reference mirror speed and $\lambda$ is the SLD 16 center wavelength). For each axial scan of the reference mirror 36, the acquired interferometric signal corresponds to a cross-correlation function of the light backscattered from the volume of (potentially moving) scatterers illuminated by the sample arm 22 probe beam, and the light returning from the reference arm 28. The interferometric signal takes the form:

$$i_d(t)=A(t)\cos[2\pi f_r t+\theta(t)] \quad \text{Equation 1}$$

Where $A(t)$ and $\theta(t)$ are the amplitude and the phase of the detected signal. Here, t is the time taken to scan the reference arm optical path length which is equivalent to scanning the sample arm length. Therefore, $$l_s=l_{so}+V_r t \quad \text{Equation 2}$$

where $l_s$ is the sample arm optical length (scan-depth into the sample) and $l_{so}$ is the scanned offset. Coherent (i.e., phase sensitive) demodulation at $f_r$ provides the complex envelope of the interferometric signal given by $i_d(t)=A(t)\exp[-j\theta(t)]$. For a mirror reflection, $i_d(t)$ becomes the source auto-correlation function and $A(t)$ and $\theta(t)=\alpha(t)$ have the information regarding the spectrum of the source. Performing a Fourier transform on the auto-correlation function provides the source power function $S_{ii}(f)$. For the SLDs or SOAs commonly in OCT systems, $S_{ii}(f)$ is approximately Gaussian and therefore $A(t)$ is also Gaussian and $\alpha(t)=0$. For a single scatterer moving with a velocity V in the sample arm, $\theta(t)=-2\pi f_s t+\alpha(t)$; where $f_s=2Vn_s\cos\phi/\lambda$ and $\phi$ is the angle between the sample probe beam and the direction of the motion of the scatterer and $n_s$ is the index of refraction for the sample. The complex envelope of the interferometric signal is given by $i_d(t)=A(t)\exp[j(2\pi f_s t-\alpha(t))]$. In this case, $i_d(t)$ becomes the cross-correlation function and the Fourier transform of this cross-correlation function provides the Doppler shifted power spectrum $S(f)=S_{ii}(f-f_s)$. When there are multiple scattering sites in the specimen, $A(t)$ and $\alpha(t)$ have the information regarding the locations of the scatterers. In this case, again $i_d(t)$ becomes a cross-correlation function and its Fourier transform is the cross-power spectrum $S_{is}(f)$. For a series of scatterers flowing with different velocities and located at different depths, $f_s$ becomes time (i.e., depth) dependent. Therefore, $$\theta(t)=-2\pi f_s(t)t+\alpha(t); \quad f_s(t)=2V(t)n_s\cos\phi/\lambda.$$

Therefore, coherent demodulation of the interferometric signal is essential to obtain both magnitude and direction of particle velocity. The complex envelope of the interferometric signal is given by $i_d(t)=A(t)\exp[j(2\pi f_s(t)t-\alpha(t))]$. Thus, $i_d(t)$ is a signal whose spectral contents change with time. Therefore, in order to obtain localized Doppler spectral (i.e., velocity) information, time frequency analysis algorithms may be used to extract the spectral content of the system as a function of time. Short-time Fourier transforms (STFT) is one time frequency analysis technique for use in the present invention. In such a case, the STFT of the detector current $i_d(t)$ will be the Doppler shifted cross power spectrum $S(t,f)=S_{is}(f-f_s(t))$. Discrete STFT of $i_d(t)$ is defined as, $$S(nt_s, f) = \sum_{m=-N/2}^{N/2-1} i_d((n+m)t_s)w(mt_s)\exp[-j2\pi fmt_s] \quad \text{Equation 3}$$

where $w(mt_s)$ is the analysis window through which the sampled time-domain demodulated detector current is shifted, $t_s$ is the sampling interval, and N is the number of samples contributing to the local spectral estimate centered at time $nt_s$. Several types of analysis windows may be used in the STFT circuit/algorithm, including rectangular, Bartlett (triangular), Tukey (which encompasses the types hamming and hanning), Blackman, Parzen, Daniall (traditional or modified), and cosine taper windows. It is well known to those skilled in the art that the choice of window may affect the amount of noise in the STFT power spectra and thus the velocity estimation accuracy.

An alternative implementation of the window is to pad the N-point analysis window with zeros on either side, increasing its length to match the number of samples in the A-scan. The total number of zeros added to the array is always L−N, where i−1 zeros are added before the N-point analysis window (for the $i^{th}$ power spectrum in the STFT), and L−N−i+1 zeros are added after the analysis window. By increasing the number of samples in the window, the frequency precision can be increased by the ratio of L/N.

Following from Equation 3, localized Doppler shifted spectra (i.e., STFT spectrograms) can thus be obtained by computing $|S(nt_s,f)|$. The mean velocity $(V(nt_s))$ of scatterers located within the segment$_s$ are estimated from the centroids $f_d(nt_s)$ of the localized Doppler spectra corresponding to each of the segments generating the mean velocity distribution profiles in the axial dimension, where, $$f_d(nt_s)=\int f|S(nt_s,f)|df/\int |S(nt_s,f)|df. \quad \text{Equation 4}$$

The equation relating the mean velocity estimate for each data segment $(V(nt_s))$ to the calculated centroid $f_d(nt_s)$ is:

$$V(nt_s)=f_d(nt_s)\times V2n_s(\cos\phi) \quad \text{Equation 5}$$

Two dimensional velocity images can thus be built up from adjacent color-coded axial velocity profiles. The color-coded Doppler display can then be merged with the gray-scale magnitude image, which describes the spatial distribution of backscatter sites in the sample.

Figure 2:
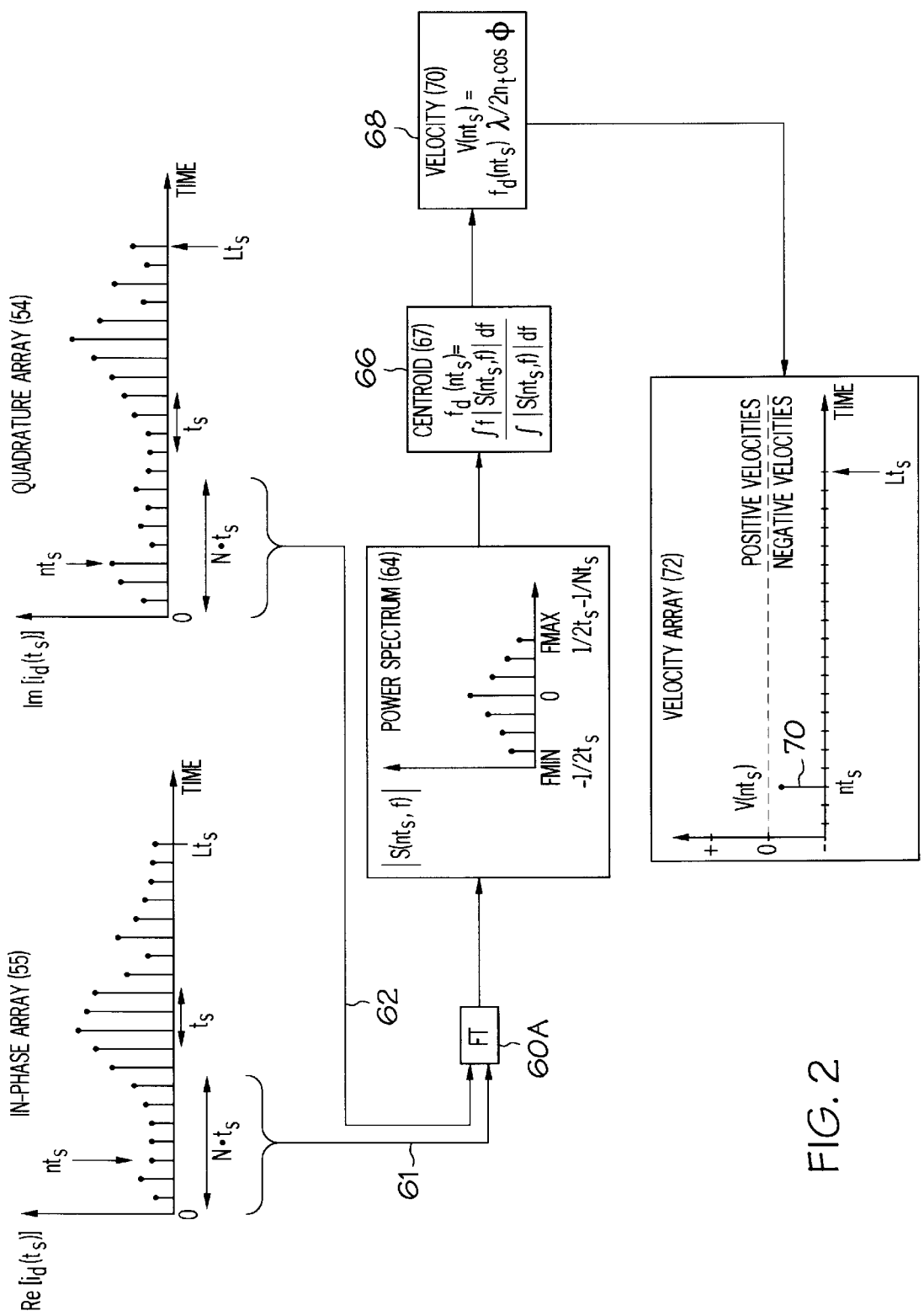
FIG. 2 is a schematic flow diagram illustrating a process of the present invention.
Figure 3:
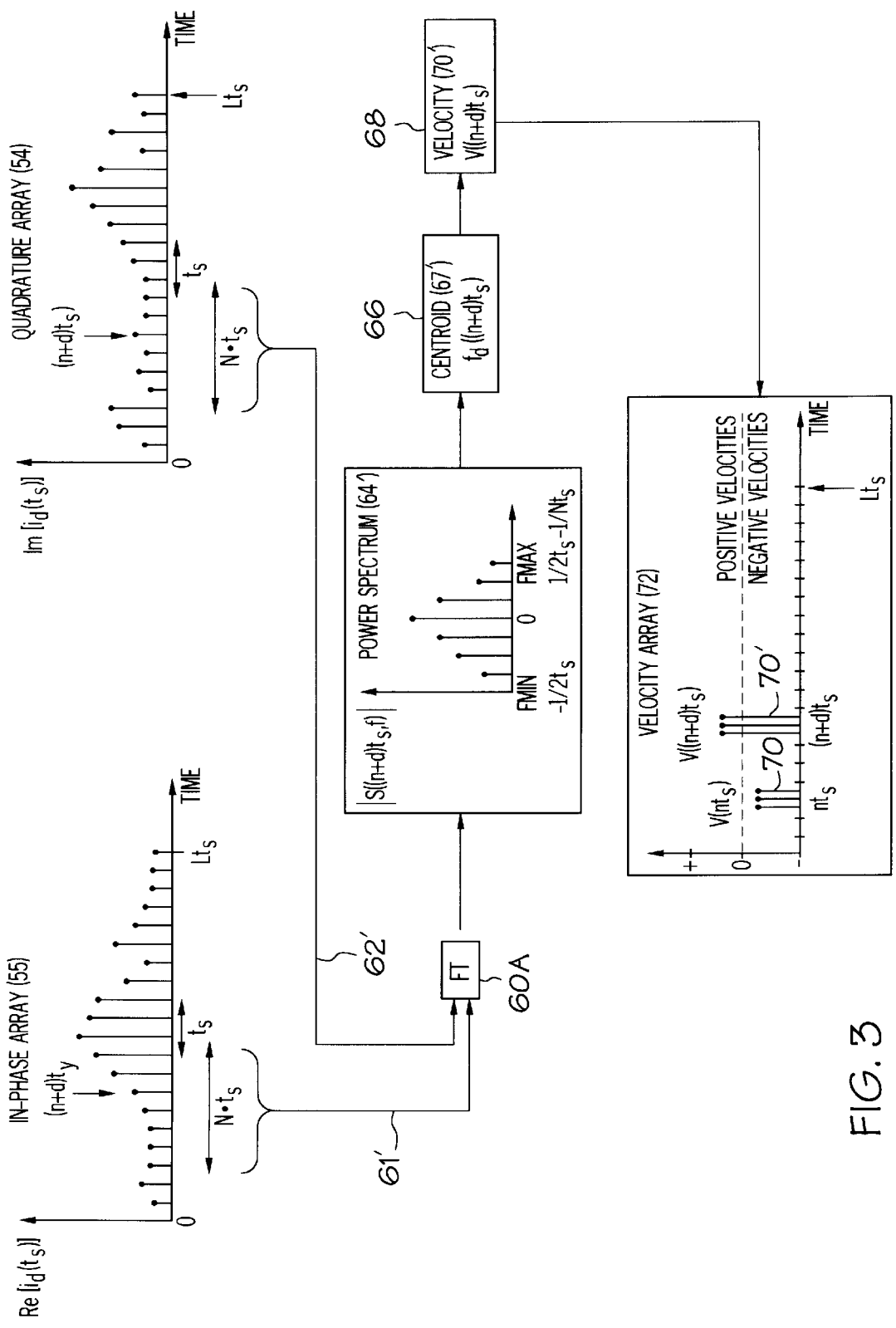
FIG. 3 is a schematic flow diagram further illustrating the process of the present invention.

Following from the above analysis, a method of the present invention for generating a Doppler OCT image is illustrated in FIGS. 1–3. Referring to FIGS. 1 and 2, as indicated by block 60, starting at time 0, a first window 61, centered at $nt_s$, of the in-phase data and a first window 62, centered at $nt_s$, of the quadrature data are respectively extracted from the in-phase array 55 and from the quadrature array 54, and are then input into a FT circuit/algorithm 60a to obtain a power spectrum 64 (a localized Doppler spectrum) for that window. The FT circuit/step 60 (FIG. 1) produces two arrays that are functions of frequency for each analysis window: an array representing the real component of the transformed interferogram data and an array representing the imaginary component of the transformed demodulated interferogram data. The power spectrum array 64 is obtained by taking the square-root of the sum of the squares of the imaginary and real arrays of transformed demodulated interferogram data.

Referring to FIG. 2, the size (time frame) of the window is indicated as $Nt_s$, which must be shorter than the entire A-scan time $Lt_s$ and is preferably longer than or equal to the coherence length of the SLD 16. Referring again to FIGS. 1 and 2, as indicated in block 66, from the power spectrum 64 a central velocity estimate 67 is calculated to obtain an estimate of the mean scatterer velocity for that window. In one embodiment of the invention this central velocity estimate is found by calculating a centroid ($f_d(nt_s)$ see Equation 4) for the power spectrum 64. As indicated in block 68, a velocity estimate value 70 ($V(nt_s)$) is obtained from the central velocity estimate (see Equation 5) and plugged into a velocity array 72 at time $nt_s$.

A limitation of the use of the centroid as a measure of the central velocity is that since all frequencies in the power spectrum are positive, the centroid of the power spectrum will always under-estimate the actual central velocity because it will necessarily include broadband noise in the centroid calculation. This inaccuracy is due to the asymmetrical distribution of noise around the Doppler shifted spectrum. In OCT, one optimally chooses the detection electronics bandwidth to match the signal bandwidth $$\Delta f = \frac{2V_r\Delta v}{c}$$

due to the reference arm Doppler shift frequency in order to achieve high reflectivity measurement sensitivity. Here, Vr is the reference arm mirror velocity, $\Delta v$ is the FWHM light source spectral bandwidth, and c is the speed of light.

However, in CDOCT the detection bandwidth is chosen to be much wider than $\Delta f$ in order to be able to measure a wide range of velocities. Since the noise power in the STFT's of segmented A-scans is always positive and the centroid calculation integrates over signals as well as noise, the centroids of the STFTs always underestimate the true Doppler shifts. The performance of the centroid calculation degrades with increasing velocities as well as with depth, where the signal attenuates in biological tissues.

An alternative central velocity estimation algorithm (called "adaptive centroid algorithm") for use with the present invention is an adaptive algorithm which locates the Doppler spectral peak, and calculates the centroid of the power only at frequencies distributed symmetrically around the peak within the Doppler width $\Delta f$. Speckle due to the presence of multiple scatterers within each coherence length in biological tissues can cause fluctuations of the Doppler shift estimate within the bandwidth $\Delta f$. Since centroids use complete information regarding the spectra, they can serve as more accurate estimates than peak locators. Although this algorithm provides accurate velocity estimates in the presence of a strong reflection in the sample arm, it fails when noise dominates signal. Therefore, a noise-recognition algorithm is utilized which calculates the average STFT power spectral density and compares it with the density near the spectral peak. The signal is considered noisy if the ratio of the average spectral density over the complete STFT and the density within a bandwidth $\Delta f$ around the peak is less than a pre-set threshold T (for example, 0.67), in which case the traditional centroid algorithm is used for central velocity estimation. This algorithm has been shown to perform well on both averaged and un-averaged STFT data, and requires a velocity computation time comparable to that of the traditional centroid method.

As shown in FIG. 3, a next window 61', shifted by a decimation factor d, centered at $(n+d)t_s$, of the in-phase data and a next window 62', centered at $(n+d)t_s$, of the quadrature data are respectively extracted from the in-phase array 55 and the quadrature array 54, and are then input into the FT circuit/algorithm 60a to obtain a power spectrum 64' for that next window. From the power spectrum 64' a central velocity estimate 67' is calculated in block 66; and from the central velocity estimate 67' a velocity estimate value 70' is calculated in block 68. The velocity estimate value 70' is plugged into d elements of the velocity array centered at time $(n+d)t_s$. The method as shown in FIG. 3 is repeated until the entire A-scan has been processed and the velocity array 72 is complete. As will be apparent to those of ordinary skill in the art, the shorter the decimation value d, the more precise the final velocity array 72 will be, in that the velocity assigned to each image pixel will more accurately reflect the STFT data centered on that pixel. On the other hand if the decimation factor d is large, then velocity pixels near the edges of the STFT segment will have their velocity estimates weighted toward the direction of the rest of the segment. Shorter decimation values, however, increase computation time since more Doppler power spectra are necessary to compute. The number of N-sample spectra computed per A-scan with L samples is $(L-N)/d$. Alternatively, it will be obvious to one of ordinary skill in the art that the decimated velocity data may be stored in a separate array smaller than the one just described, and later magnified before being overlayed onto the grayscale image.

By utilizing the coherent demodulation, described above, the velocity estimate values 70,70' will have both a sign and a magnitude, where the particular sign corresponds to particular (opposing) travel directions of the scatterers within the sample. As indicated in block 74 (FIG. 1), from the velocity array 72, a color velocity image will be processed and combined with, or overlayed onto the gray-scale image 58. The velocity image processing will include a step of assigning one of two colors to image pixels in a velocity profile corresponding to the depth into the sample represented by the windows 61, 61'. In one embodiment of the invention, the velocity profile is an array of image pixels corresponding to the particular A-scan. Which of the two colors is assigned depends upon the sign (i.e., blue for positive and red for negative) of the velocity estimate values 70, 70'. Additionally, the shade or the level of brightness, density or intensity for that selected color is adjusted according to the magnitude of the velocity estimate values 70, 70'.

Figure 4:
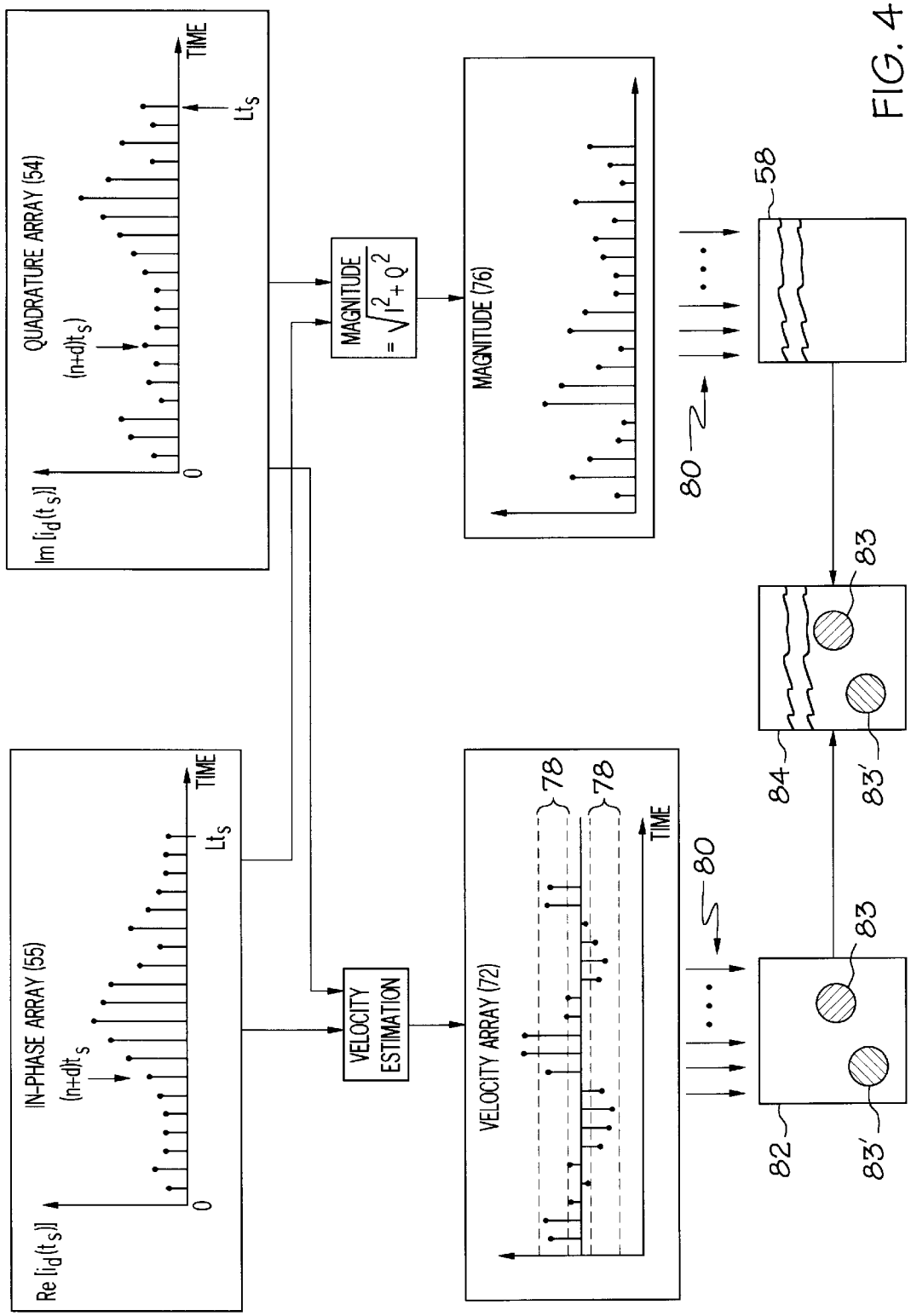
FIG. 4 is a schematic flow diagram further illustrating the process of the present invention.

As shown in FIG. 4, the in-phase array 55 and quadrature array 54 from each A-scan are used to calculate a velocity array 72 and a magnitude array 76 as discussed above. As also discussed above, different colors can be designated for the positive and negative data from the velocity array, which will correspond to the different directions of scatterer movement within the sample. Before assigning the colors to the data in the velocity array, the user may be prompted to select both positive and negative, minimum threshold and maximum saturation velocities 78. These threshold and saturation velocities 78 are then applied to the velocity array 72 or to the velocity profile to provide an upper and lower bound to the velocity display color scale which allows all desired velocities to be displayed. Velocities which are larger than the maximum positive and negative saturation velocities, respectively, may be rendered the same color (brightness, shade, etc.) as the positive or negative maximum saturation velocities themselves, or else may be rendered in some other distinctive color (brightness, shade, ect.) in order to indicate that the velocity color scale was saturated at that location. Velocities which are smaller than the positive and negative threshold velocities are rendered as transparent to indicate that flow was not detected in that image region, and to allow for visualization of the underlying gray-scale magnitude reflectivity image. It will also be apparent to those of ordinary skill in the art that the threshold and saturation velocities 78 may be predetermined in the DSP 56 or may be automatically determined by the DSP 56 according to predetermined guidelines or algorithms.

As indicated by the multiple arrows 80, multiple A-scans are taken for different lateral positions of the sensor probe 30 along the sample 32 and the multiple velocity arrays 72 and the multiple magnitude arrays 76 are used to respectively create a two-dimensional, colorized velocity image 82 and a two-dimensional, gray-scale image 58 pertaining to backscatter positions within the sample. The two dimensional velocity image may be created by aligning velocity profiles side-by-side to create a two-dimensional colorized Doppler image 82 indicating the direction and velocity of moving scatterers within the sample. In the velocity image 82 fluid flow in a first direction is indicated by a first color 83 and fluid flow in an opposite direction is indicated by a second color 83'. These images are then merged to create a colorized Doppler OCT image of the sample 84. One way to merge the velocity image 82 with the gray-scale image 58 is to overlay the velocity image onto the gray-scale image.

Figure 10:
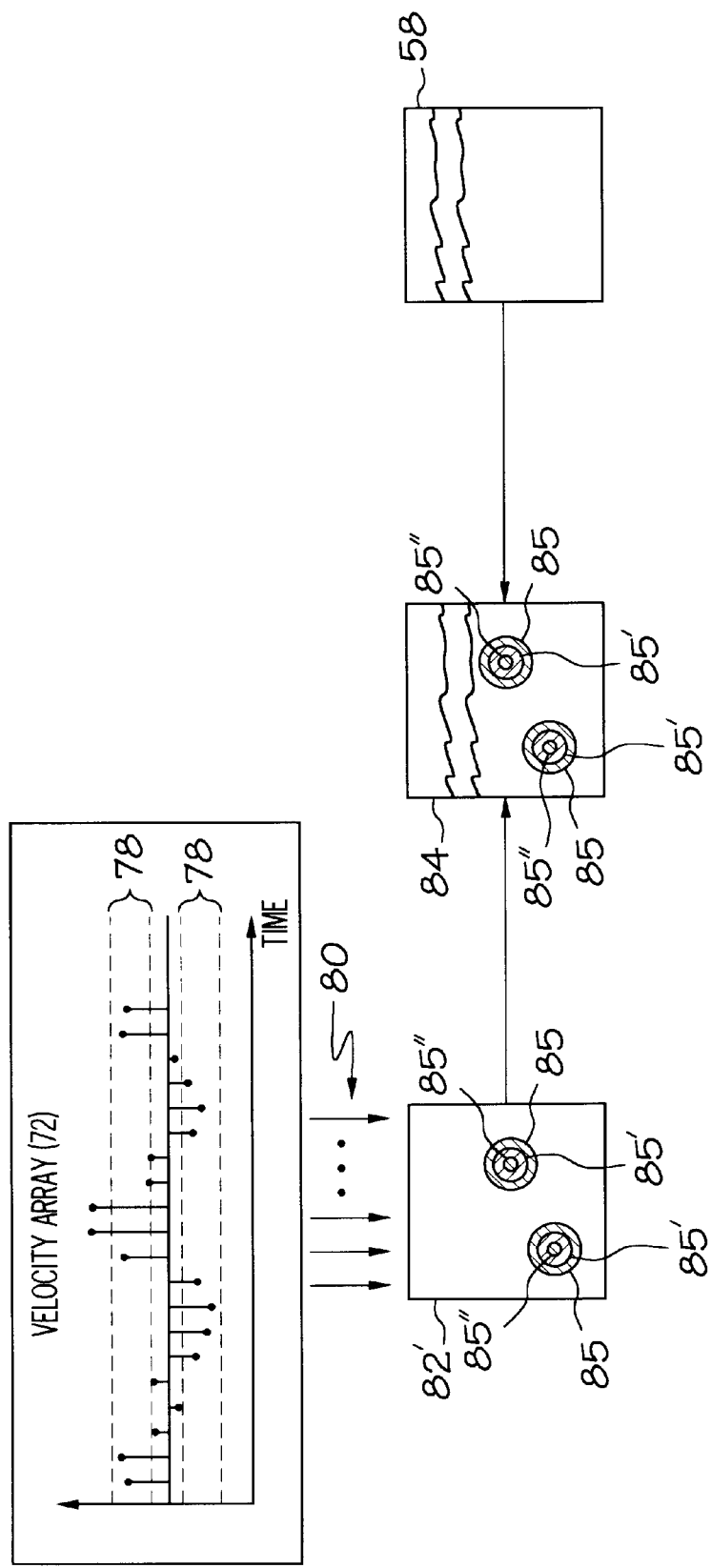
FIG. 10 is a schematic flow diagram illustrating another alternate process and system of the present invention.

The present invention provides at least two separate embodiments of color coding of velocity information. In the first, described above (FIG. 4), the two colors or hues are selected to reflect the sign of the velocity. The intensity, shade, brightness, or density of the color then reflects the magnitude of the velocity estimate. In this color scheme, which is commonly used in color Doppler ultrasound displays, a blood vessel appears as a red or blue (for example) disk or oval which is brightest in the center (reflecting that the highest velocities are in the center), and fades in brightness toward the edges of the vessel. As shown in FIG. 10, an alternate scheme for color coding of velocity information to produce a colorized velocity image 82', which may offer some advantages in image rendering speed and ease of interpretation, assigns a specific color or shade 85, 85', 85" to each velocity, and encodes into the magnitude of the signal into the brightness of the specific color or shade 85, 85', 85" (or equivalently, the reflectivity of the tissue at that site). In this scheme, a blood vessel would appear as a series of concentric rings, whose radius is smallest at the vessel's center. Assuming one of the techniques described herein (STFTs, NBPFs, or multiple demodulators) is used to obtain an estimate of the frequency power spectrum for each analysis region in the sample, the central velocity for that analysis region is estimated either by choosing the velocity with the highest magnitude, or else by using a centroid or adaptive centroid (as described above) algorithm. If this velocity is above the threshold and below the saturation velocity specified by the user, it is encoded into a color and overlayed on the gray-scale magnitude image 58 for that analysis region.

Accordingly, the OCT image created by the present invention will not only be able to display tissue layers of the biological samples to cellular resolution, it will also have the capability of providing a correlation between the locations of blood vessels and other fluid flows using color Doppler OCT. Therefore, the present invention provides micron-scale resolution color Doppler OCT mapping of bidirectional blood flow and sub-surface vessels in vivo and has the potential applications in retinal perfusion mapping, management of bleeding in ulcerative conditions, and in tissue necrosis evaluation.

It has been shown, mathematically, in M. D. Kulkarni, T. G. van Leeuwen, S. Yazdanfar, and J. A. Izatt, "Velocity-Estimation Accuracy and Frame Rate Limitations in Color Doppler Optical Coherence Tomography," Optics Letters 23, in press (1998), that a better velocity estimate can be obtained for a particular position in the sample by taking multiple A-scans for that lateral position and then averaging the central velocity of the averaged spectrum. Accordingly, in one embodiment of the invention, multiple A-scans are taken for each position of the sample arm, and the power spectrum estimates calculated for each A-scan taken are averaged together to produce a more accurate power spectrum estimate for that particular lateral position of the sample arm. In another embodiment of the invention, multiple A-scans are taken for each lateral position of the sample arm, and the velocity estimates calculated for each A-scan taken are averaged together to produce a more accurate velocity estimate for that particular lateral position of the sample arm.

It is also known that the spatial resolution of the velocity estimate is limited by the window size ($Nt_s$), the larger the window—the lower the spatial resolution. But according to the following equation governing the velocity estimate, $$V_s^{min} = \frac{\lambda_0}{2n_t\cos\theta} \cdot \frac{1}{Nt_s}$$

velocity resolution is inversely related to the window size, the larger the window—the better the velocity resolution. Accordingly, two alternate embodiments of the invention overcome this trade-off and provides for simultaneous high spatial resolution and high velocity resolution. This is done, in a general sense, by slowing down the time for taking the A-scan.

Figure 5:
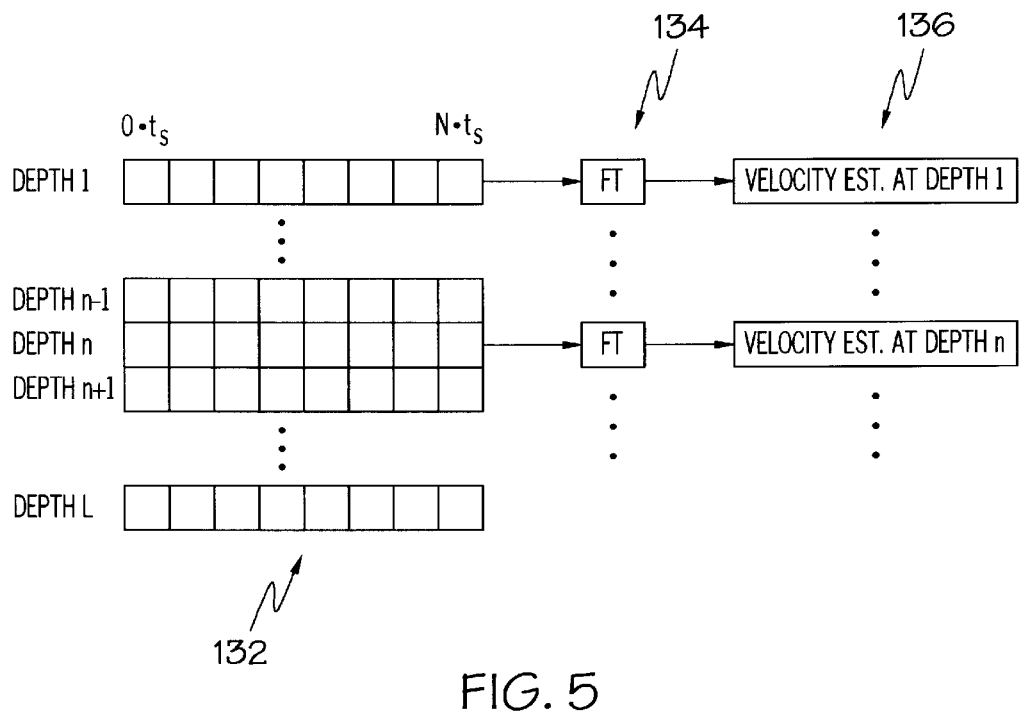
FIG. 5 is a schematic flow diagram illustrating an alternate process and system of the present invention.
Figure 6:
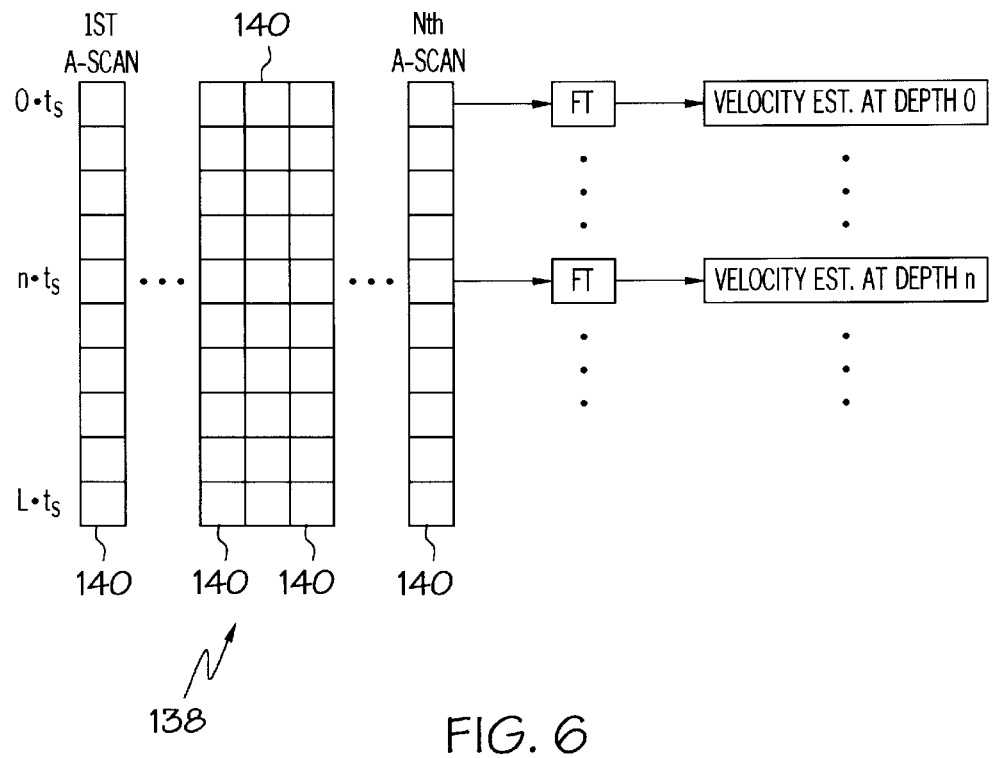
FIG. 6 is a schematic flow diagram illustrating another alternate process and system of the present invention.

In a first alternate embodiment, illustrated in FIG. 5, for each position n of the reference arm, instead of one set of in-phase and quadrature data taken, N acquisitions of in-phase and quadrature data are taken as indicated by step 132 (where N corresponding to the window size). As indicated in step 134, each set of N acquisitions of in-phase and quadrature data at depth n is plugged into a short-time Fourier transform circuit/algorithm. As indicated in step 136, from the output of the short-time Fourier transform circuit/algorithm, a velocity estimate at depth n is determined. Thus the number of data acquisitions at depth n, and the length of time that the reference arm must remain at the position corresponding to depth n, corresponds to the window size N. Thus, instead of calculating a velocity estimate for a window pertaining to multiple positions of the reference arm, the velocity estimate is calculated for a window pertaining to a single position (depth) of the reference arm.

With this alternate embodiment, it is not necessary to take the multiple sets of data at a single position n of the reference arm, so long as the multiple readings are taken at within a range of reference arm movement from position n that is less than the coherence length of the SLD source 16. Accordingly, the reference arm movement does not need to be stopped so that multiple readings can be taken while the reference arm is at a given position. But the reference arm velocity must be set to a certain speed, or must be repeatedly scanned (dithered) over a small distance, such that the multiple readings are taken before the reference arm has moved as far as the coherence length of the SLD source 16.

In a second alternate embodiment, instead of one A-scan being taken for each lateral position of the sample arm, N A-scans are taken for each lateral position of the sample arm. The in-phase and quadrature data are then arranged into a two-dimensional matrix 138 by aligning the one-dimensional (vertical) matrices for each A-scan 140 taken side-by-side. Thus, instead of calculating a velocity estimate for a window pertaining to multiple positions of the reference arm (a vertical "column" window), the velocity estimate is calculated for a single position (a horizontal "row" window) of the reference arm.

Referring again to the embodiment as shown in FIG. 1, it will be apparent to one of ordinary skill in the art, and it is within the scope of the present invention to skip the coherent demodulation step or circuit 50, converting the filtered interferogram data 49 into digital data using an A/D circuit or step, and then introducing the non-demodulated and digitized interferogram data into the digital signal processing circuit. In such a system, the output of the short-time Fourier transform step 60 will be a power spectrum centered at the Doppler shift frequency of the reference arm $f_r$. Therefore, in the velocity calculation, the Doppler shift frequency of the reference arm must be subtracted out as follows:

$$V(nt_s) = (f_d(nt_s) - f_r) \times \lambda / 2n_s(\cos\phi) \qquad \text{Equation 6}$$

where $f_r$ is the Doppler shift frequency of the reference arm.

As mentioned above, referring again to FIG. 1, the data acquisition system may optionally include a high-coherence calibration interferometer 14 to accurately monitor and compensate for the inevitable velocity fluctuations in the reference mirror 36. The calibration interferometer 14 includes a long-coherence length, narrow-band laser illumination source 86, such as a helium neon (He—Ne) laser or a distributed feed-back diode laser (DFB diode laser), a reference probe 88 and a sample probe 90. The narrow-band illumination source must have a coherence length that is longer than the region (depth) in the sample 32 that is being scanned (for example, the He—Ne laser has a coherence length of several meters).

The illumination source 86 transmits to a beam splitter 92, which separates the source signal into two illumination source signals, one being transmitted to the reference probe 88 and the other to the sample probe 90. The reference probe 88 focuses its illumination source signal to a mirror 36' mounted facing backwards on the same mount as the reference mirror 36. The sample probe 90 focuses its illumination source signal to a fixed mirror 94. The interferometer 14 also includes a photodetector 96 for receiving the combination of light reflected back from the translating mirror 36' and the fixed mirror 94, and for producing an analog signal 98 corresponding to the intensity of light received. Because the long-coherence length illumination source 86 is used, the analog interferometric signal 98 produced by the photodetector 96 will be a relatively constant amplitude sinusoidal signal, having a frequency equal to the Doppler shift corresponding to velocity fluctuations in the translating mirror 36' (the reference mirror) experienced by the electric field in the reference arm.

The analog signal 98 produced by the photodetector 96 is sent to an interval-detect circuit/device 100 for detecting features in the analog signal 98 that are regular in time (i.e., zero crossings) and for outputting a signal 102 indicative of such features. The feature indicative signal 102 is fed into a clock generator circuit/device 104 for generating a digital clock source signal 106 for clocking (triggering) the analog to digital converters 53 discussed above. Thus, the sampling rate of the analog-to-digital converters 53 will be synchronized according to the fluctuations in the reference mirror 36 translation velocity detected by the calibration interferometer 14. Referring to U.S. patent application Ser. No. 09/040, 128, filed Mar. 17, 1998, discussed above, it will be apparent to those of ordinary skill in the art that there are a number of alternate systems and methods available for synchronizing the processing of the interferogram data according to the inevitable fluctuations in reference arm velocity.

In another alternate embodiment of the present invention, the necessity of a short-time Fourier transform step 60 to produce the power spectrum 64 may be eliminated by utilizing a bank of narrow-band band-pass filters ("NPBFs"), where each NBPF passes a particular frequency along the power spectrum frequency scale.

Figure 7:
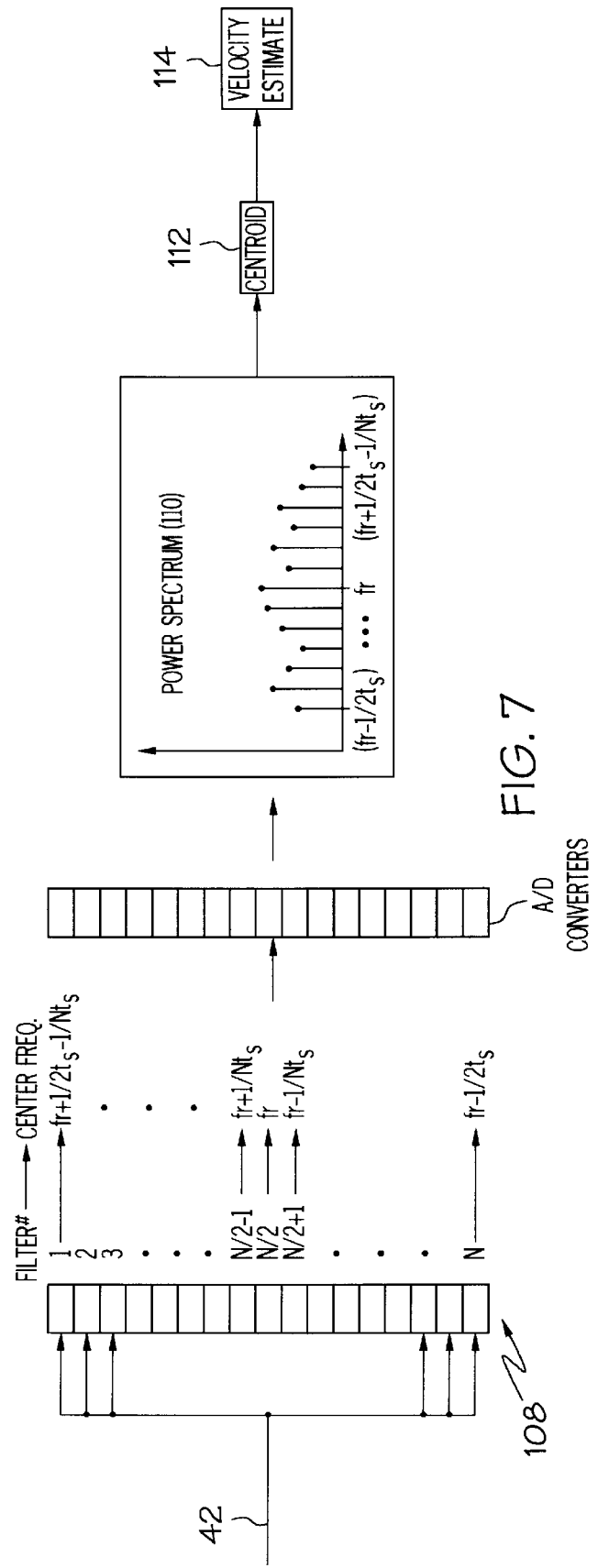
FIG. 7 is a schematic flow diagram illustrating another alternate process and system of the present invention.

As shown in FIG. 7, a bank of NBPFs 108 may be positioned to filter the raw, (non-demodulated) photodetector signal 42. The bank 108 comprises N NBPFs, each having a bandwidth of approximately $1/Nt_s$, where the center frequency of each NBPF corresponds to a particular frequency along the frequency scale of a power spectrum 110, optionally centered at the Doppler shift frequency of the reference arm. In this implementation, $t_s$ corresponds to the sampling interval of an array of N A/D converters placed either before the bank of NBPFs (if the NBPFs are implemented digitally), or after the bank of NBPFs (if the NBPFs are implemented in analog electronics). Thus, half (or some other fraction) of the NBPFs will pass frequencies below the Doppler shift frequency of the reference arm $f_r$, and the other half (or the remaining fraction) will pass frequencies above the reference arm Doppler shift frequency $f_r$. In one example, the middle NBPF will be centered at the reference arm Doppler shift frequency, $f_r$; the next NBPF above the center NBPF will be centered at the frequency $f_r+1/Nt_s$; and the next NBPF below the center NBPF will be centered at the frequency $f_r-1/Nt_s$. From this power spectrum 110, the centroid 112 and velocity estimate 114 will be determined as discussed above in Equations 4 and 6. In this alternate embodiment, the coherent demodulation circuit/device 50 and the short-time Fourier transform circuit/step 60 are not needed. This alternative embodiment is mathematically equivalent to the STFT, since Equation 3 can be re-written as $$S(nt_s, f) = \tilde{i}_d(nt_s) \otimes w(n)t_s \exp(j2\pi f n t_s), \qquad \text{Equation 8}$$

where $\otimes$ represents convolution. In general, the analysis window is the impulse response of a low-pass filter. Therefore, multiplying it by the exponential in Equation 8 results in a band-pass filter. Its convolution with the interferometric signal can then provide the same information as the STFT.

Figure 8:
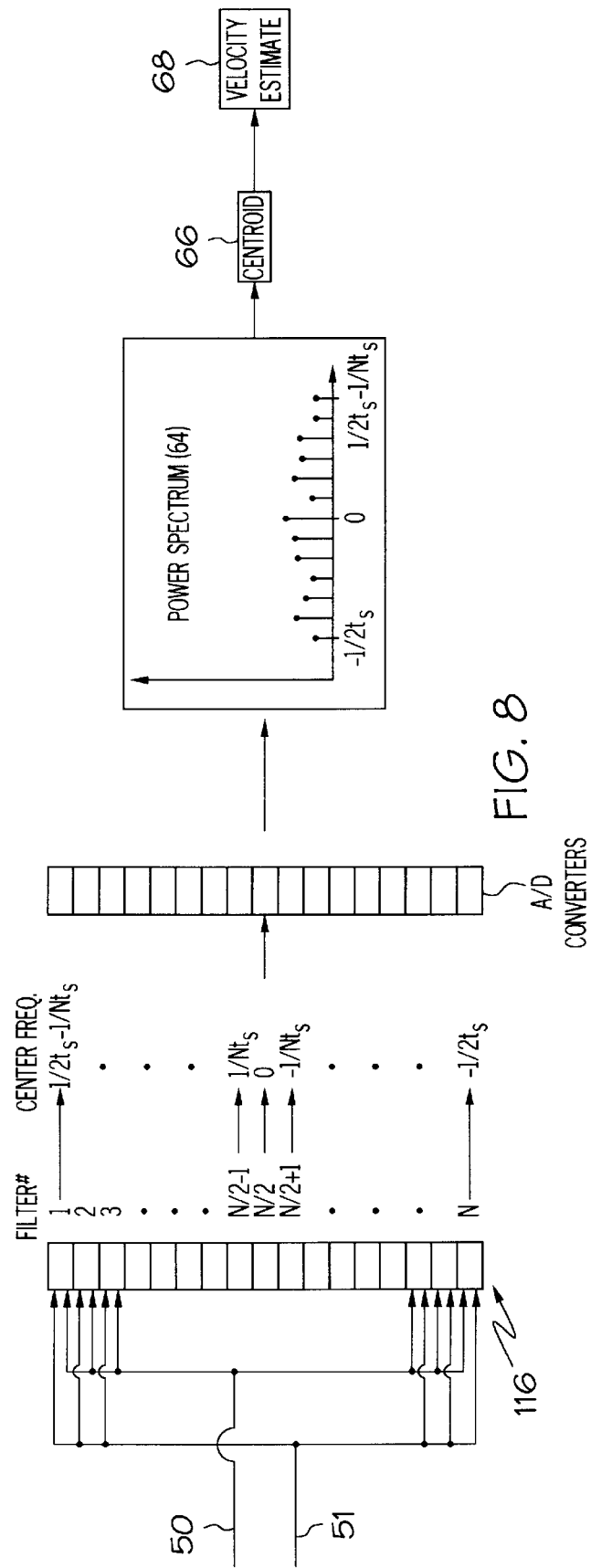
FIG. 8 is a schematic flow diagram illustrating another alternate process and system of the present invention.

Alternatively, as shown in FIG. 8, a bank of complex NBPFs 116 may be positioned after the coherent demodulation circuit/device 50, where each receives both the analog in-phase "I" data 51 and the analog quadrature "Q" data 52. The bank 116 comprises N NBPFs, each having a bandwidth of approximately $1/Nt_s$, where the center frequency of each NBPF corresponds to a particular frequency along the frequency scale of the power spectrum 64 centered at zero frequency. In this implementation, $t_s$ corresponds to the sampling interval of an array of N A/D converters placed either before the bank of NBPFs (if the NBPFs are implemented digitally), or after the bank of NBPFs (if the NBPFs are implemented in analog electronics). Thus, half (or some other fraction) of the NBPFs will pass frequencies below zero, and the other half (or the remaining fraction) will pass frequencies above zero. The middle NBPF will be centered at zero frequency; the next NBPF above the center NBPF will be centered at the frequency $1/Nt_s$; and the next NBPF below the center NBPF will be centered at the frequency $-1/Nt_s$. From this power spectrum 64, the central velocity estimate (centroid) 66 and velocity estimate 68 will be determined as discussed above in Equations 4 and 5. In this alternate embodiment, the short-time Fourier transform circuit/step 60 is not needed. It will be apparent to one of ordinary skill in the art that the array 116 of complex NBPFs may be replaced by two arrays of NBPFs, one array for the in-phase data 51, and one array for the quadrature data 52; and the square-root of the sum of the squares of the output of each array will yield the resultant power spectrum 64. In this alternative embodiment, Equation 8 is applied to the demodulated data rather than the complex interferometric signal.

Figure 9:
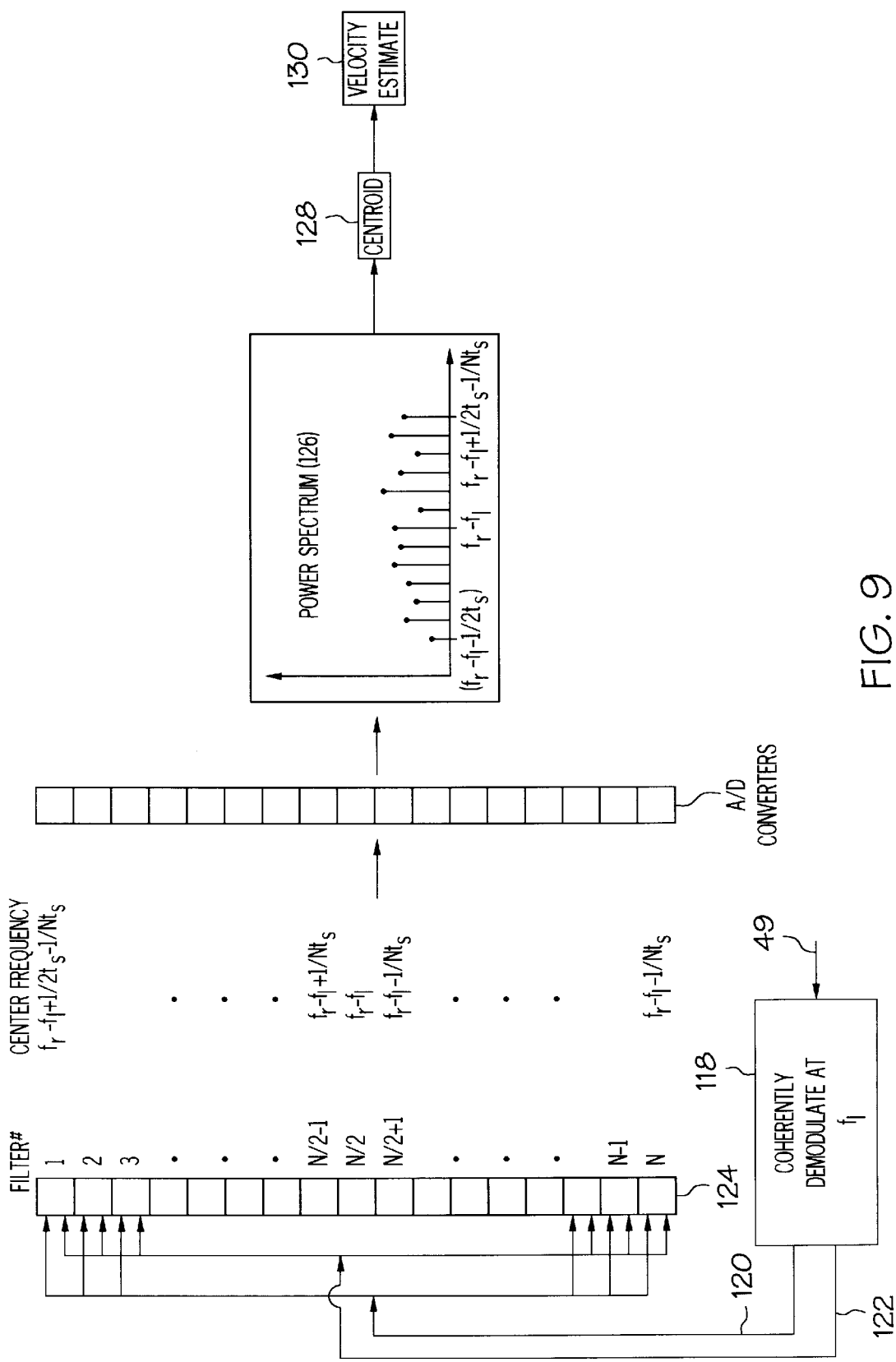
FIG. 9 is a schematic flow diagram illustrating another alternate process and system of the present invention.

As shown in FIG. 9, the interferometer data 49 can be coherently demodulated at frequency $f_I$, as shown in block 118, to produce in-phase data 120 and quadrature data 122. The in-phase and quadrature data 120, 122 is fed into a bank of complex NBPFs 124. The bank 124 comprises N NBPFs, each having a bandwidth of approximately $1/Nt_s$, where the center frequency of each NBPF corresponds to a particular frequency along the frequency scale of a power spectrum 126 optionally centered at frequency $f_r-f_I$. In this implementation, $t_s$ corresponds to the sampling interval of an array of N A/D converters placed either before the bank of NBPFs (if the NBPFs are implemented digitally), or after the bank of NBPFs (if the NBPFs are implemented in analog electronics). Thus, half (or some other fraction) of the NBPFs will pass frequencies below $f_r-f_I$, and the other half (or the remaining fraction) will pass frequencies above $f_r-f_I$. In one example, the middle NBPF will be centered at $f_r-f_I$, the next NBPF above the center NBPF will be centered at the frequency $f_r-f_I-1/Nt_s$; and the next NBPF below the center NBPF will be centered at the frequency $f_r-f_I-1/Nt_s$. From this power spectrum 126, the centroid 128 will be determined as discussed above in Equations 4 and the velocity estimate will be determined according to the following equation:

$$V(nt_s) = (f_d(nt_s) - f_I) \times \lambda/2n_s(\cos \phi) \quad \text{Equation 9}$$

In this alternate embodiment, the short-time Fourier transform circuit/step 60 is not needed. It will be apparent to one of ordinary skill in the art that the array 124 of complex NBPFs may be replaced by two arrays of NBPFs, one array for the in-phase data 120, and one array for the quadrature data 122; and the square-root of the sum of the squares of the output of each array will yield the resultant power spectrum 126. The frequency $f_I$ is selected such that the NBPFs are centered in the kHz frequency range. Such NBPFs are cheaper, and more readily available than NBPFs centered in the frequencies near the reference arm Doppler shift frequency $f_r$.

It should be obvious to those of ordinary skill in the art that the approach of using a bank of NBPF's or demodulators to obtain spatially-localized frequency information is quite general, and is not necessarily limited to the case of using all NBPF's symmetrically distruabuted around the reference arm Doppler shift frequency (as in FIG. 7), or around baseband (as in FIG. 8), or at evenly spaced frequencies (as in both FIGS. 7 and 8), or even all with the pass bandwidth. The user may have the option to select any frequency to monitor, with any bandwidth desired.

An alternative embodiment of the invention employs multiple coherent demodulators operating in parallel in order to obtain an estimate of the power spectrum for a given analysis region in the sample.

In equation 3, the exponential term can be grouped with the detector current, such that $$S(nt_s, f) = \exp(j2\pi fnt_s) \cdot \left[ \sum_{m=-N/2}^{N/2-1} i_d[(n+m)t_s]\exp[-j2\pi f(n+m)t_s]w(mt_s) \right]$$

Inside the brackets is a convolution summation between the demodulated detector current a low-pass filter:

$$S(nt_s, f) = \exp(j2\pi fnt_s) \cdot [i_d(nt_s)\exp(-j2\pi fnt_s) \otimes w(nt_s)]$$

Here the STFT is a convolution between the demodulated detector current and the analysis window, or the operation performed by a quadrature detector at a single frequency. The output is then modulated by $\exp(j2\pi fnt_s)$. For CDOCT, this final step may be diregarded, since sythesis (reconstruction of the signal from the STFT) is not necessary. Hence, time-frequency analysis can be implemented with parallel demodulation electronics. This alternative approach offers several advantages for the acquisition of local spectral information. First, the output of each of the detection channels is nearly instantaneous, allowing for real-time implementation of CDOCT. It avoids time-consuming calculations of Fourier transforms used in Doppler processing with the STFT. Second, the electronic components necessary to implement this approach (e.g., low-pass filters and demodulators) are readily available. Finally, low-pass filters are preferable to band-pass filters due to more reliable phase responses of the latter.

Figure 11:
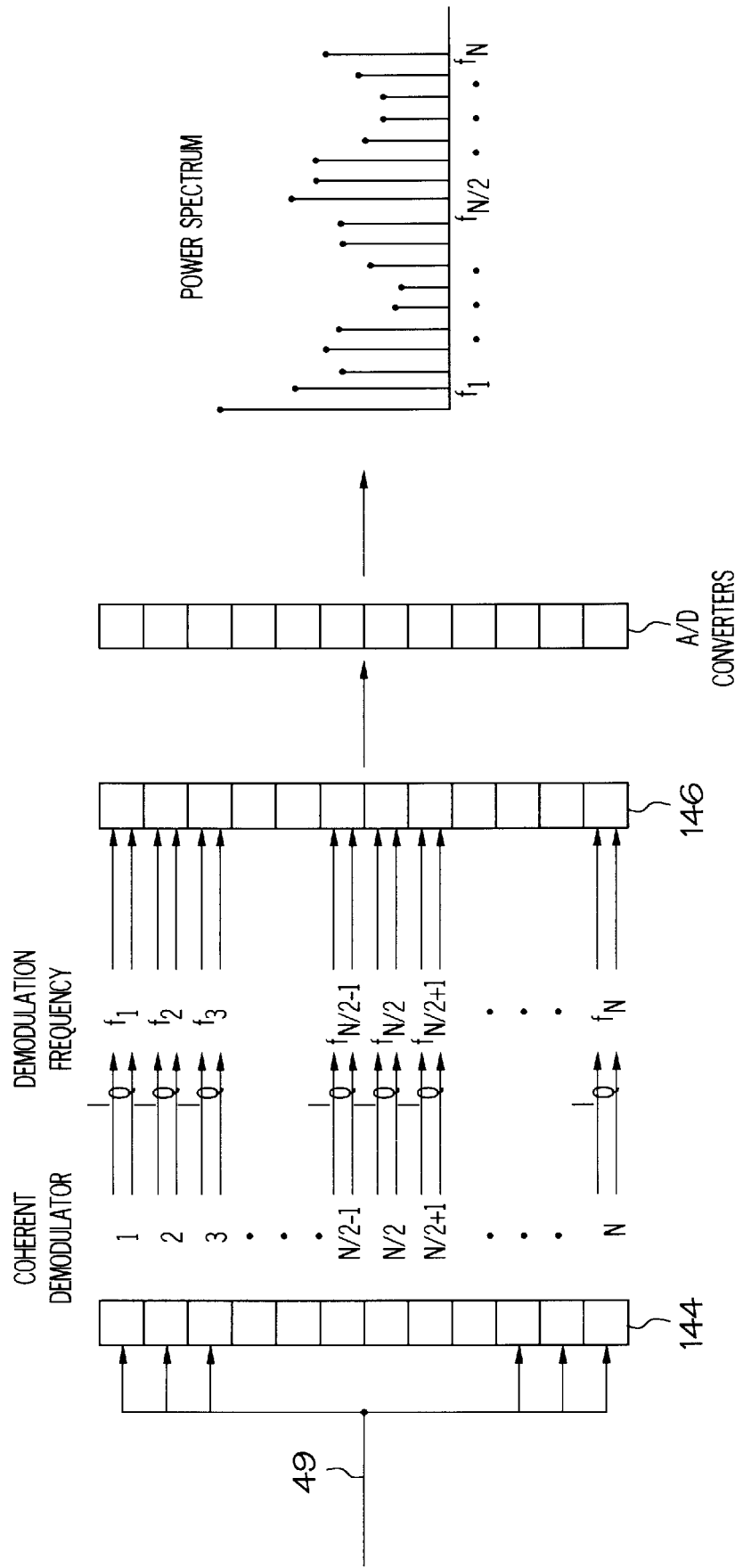
FIG. 11 is a schematic flow diagram illustrating another alternate process and system of the present invention.

In this embodiment, illustrated in FIG. 11, the raw 42, or preferably band-pass-filtered 49 detector signal is split and sent to N parallel coherent demodulators 144, with user-specified frequencies ranging from $f_1$ to $f_N$. Each of these demodulators 144 transfers the content of the interferometric signal at its own demodulation frequency down to baseband. Each demodulator is followed by a low-pass filter 146 with cutoff frequency determined by the optimal bandwidth $\Delta f$, given by Equation 7. From the output of the low-pass filters 146, a power spectrum 148 is generated; and from the power spectrum 148, the central velocity estimate will be calculated as discussed above. It is to be understood that $f_{N/2}$ could be the Doppler shift frequency $f_r$. It is also to be understood that spacing of demodulator frequency may be arbitrary.

Figure 12:
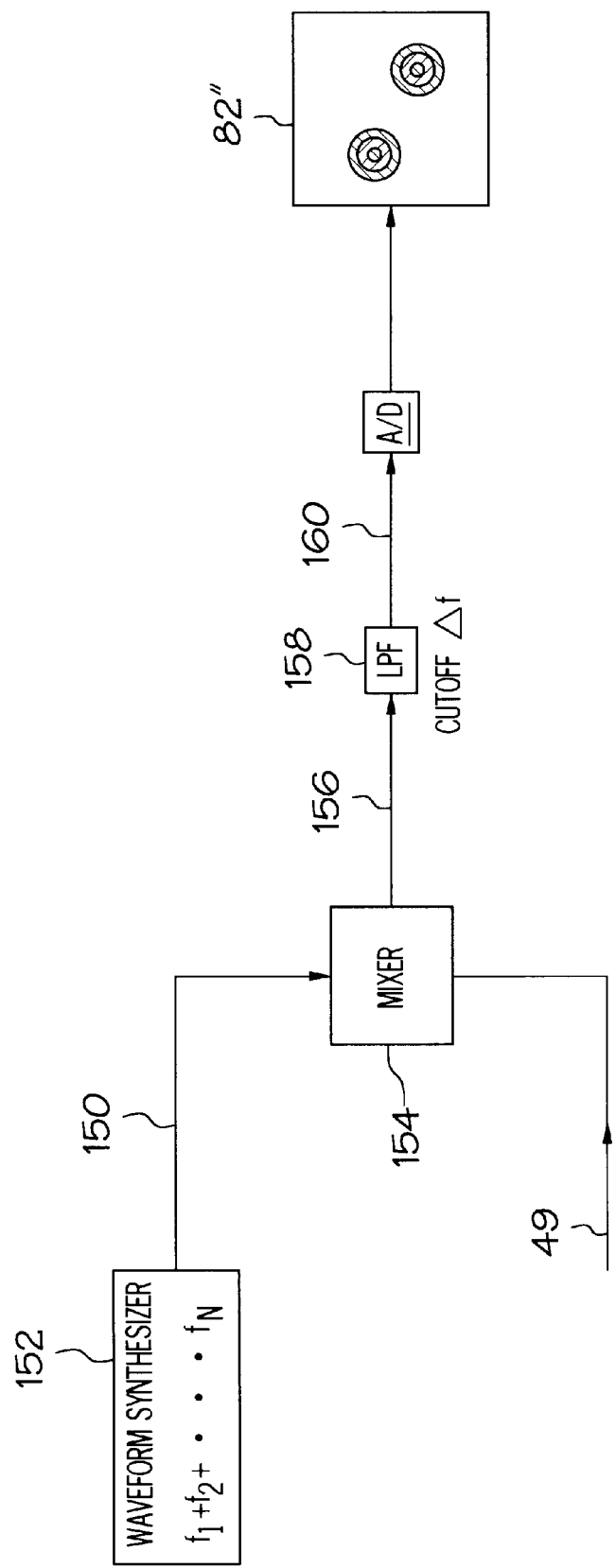
FIG. 12 is a schematic flow diagram illustrating another alternate process and system of the present invention.

Another alternative embodiment, illustrated in FIG. 12, allows for simultaneous demodulation of multiple frequencies using a synthesized demodulating waveform, a mixer and a low-pass filter. This embodiment represents a substantial savings in the number of frequency mixers and low-pass filters required, although it does not provide estimation of the complete frequency spectrum within each analysis region. In this embodiment, a reference waveform 150 is synthesized by a waveform synthesizer 152 as a sum of a desired number of sinusoids at frequencies ranging from $f_1$ to $f_N$. These frequencies are mixed in a mixer 154 with the raw 42, or preferably band-pass filtered 49 detector signal, and the resulting mixed signal 156 is then low-pass filtered in a low-pass filter 158 with cutoff frequency $\Delta f$. The complex envelope of the signal after mixing can be expressed as $$i_d(t) = A(t)\exp\left[-j2\pi t\left\{f_r - f_s - \sum_{i=1}^{N} f_i + \phi(t)\right\}\right]$$

The resulting low-pass filtered signal 160 is then digitized and displayed in a velocity image 82", and will approximate a "rings" display. The spacing of the discrete components of the reference waveform should be equal to or greater than $\Delta f$ to prevent overlapping information from two demodulation frequencies.

A separate method for real-time estimation of the velocity and degree of turbulence in flow detected by CDOCT is now described. This method has substantial advantages in the amount of computation time and memory required as compared to methods based on the STFT. This method is based on a real-time auto-correlation calculation which can be implemented in analog electronics, requiring only the digitization, storage, and display of only the velocity data. The disclosed auto-correlation method is based on a mathematical derivation which estimates the central velocity and turbulence of the fluid flow in the sample as being related to the first and second moments of the Doppler-shifted frequency power spectrum, respectively:

$$\bar{\omega} = \frac{\int_{-\infty}^{\infty} \omega P(\omega)d\omega}{\int_{-\infty}^{\infty} P(\omega)d\omega}, \quad \text{Equation 10}$$

$$\sigma^2 = \frac{\int_{-\infty}^{\infty} (\omega - \bar{\omega})^2 P(\omega)d\omega}{\int_{-\infty}^{\infty} P(\omega)d\omega}. \quad \text{Equation 11}$$

Equation 10 is the same equation as equation 4 above, except that $\omega = 2\pi f$ is defined as angular frequency and $P(\omega) = P(2\pi f) = |S(t, 2\pi f)|^2$ is identified as the detector current power spectrum corresponding to a specified analysis region corresponding to the reference mirror position within a specified time window centered at time t. As before, the mean velocity estimate for each time window is related to the centroid frequency by $$V = \frac{\bar{\omega}}{2\pi} \frac{\lambda}{2n_s \cos\phi}.$$ Equation 12

The well-known Weiner-Khinchin theorem of information theory states that the auto-correlation $R(\tau)$ of any signal waveform is given by the inverse Fourier transform of the signal's power spectral density $P(\omega)$:

$$R(\tau) = \int_{-\infty}^{\infty} P(\omega)e^{j\omega\tau} d\omega,$$ Equation 13 where $\tau$ is called the "lag" of the auto-correlation. Defining the derivative of equation 13 with respect to $\tau$ as $\dot{R}(\tau)$, evaluating this derivative for the case when the lag $\tau=0$, and inserting the result into equations 10 and 11 yields the following expressions:

$$\omega = \frac{-j\dot{R}(0)}{R(0)},$$ Equation 14

$$\sigma^2 = \left\{\frac{\dot{R}(0)}{R(0)}\right\}^2 - \frac{\ddot{R}(0)}{R(0)}.$$ Equation 15

Thus, in words, the central velocity estimate is obtained from the zero-lag element of the auto-correlation function of the interferometric detector current and its first derivative. Similarly, an estimate of the flow turbulence is obtained from the zero-lag element of the auto-correlation function of the interferometric detector current and its first and second derivatives.

An algorithm to take advantage of these mathematical relationships is based on the assumption that the auto-correlation function of equations 13–15 has the form:

$$R(\tau) = A(\tau)e^{j\phi(\tau)},$$ Equation 16 where $A(\tau)$ is assumed to be a real, even function of $\tau$ and $e^{j\phi(\tau)}$ is assumed to be an odd function of $\tau$. Under these assumptions, it follows that:

$$\dot{R}(\tau) = [\dot{A}(\tau) + jA(\tau)\dot{\phi}(\tau)]e^{j\phi(\tau)}.$$ Equation 17

Plugging in for the zero-lag element of $R(\tau)$ leads to $$\dot{R}(0) = [\dot{A}(0) + jA(0)\dot{\phi}(0)]e^{j\phi(\tau)},$$ Equation 18 which under the assumptions of the evenness of $A(\tau)$ and the oddness of $e^{j\phi(\tau)}$ leads to $$\dot{R}(0) = jA(0)\dot{\phi}(0),$$ Equation 19

$$R(0) = A(0).$$ Equation 20

Therefore, using equation 19 and 20 in equation 14 gives the result:

$$\bar{\omega} = \dot{\phi}(0) \approx \frac{\phi(T) - \phi(0)}{T} = \frac{\phi(T)}{T},$$ Equation 21 where $\tau = T$ denotes the time delay of the first lag element of the auto-correlation function. In practice, this time delay is set by the length of a delay line used to implement this algorithm as shown below.

By a similar mathematical reasoning, it is possible to show that $$\sigma^2 = \frac{1}{T^2}\left\{1 - \frac{|R(T)|}{R(0)}\right\}.$$ Equation 22

Figure 13:
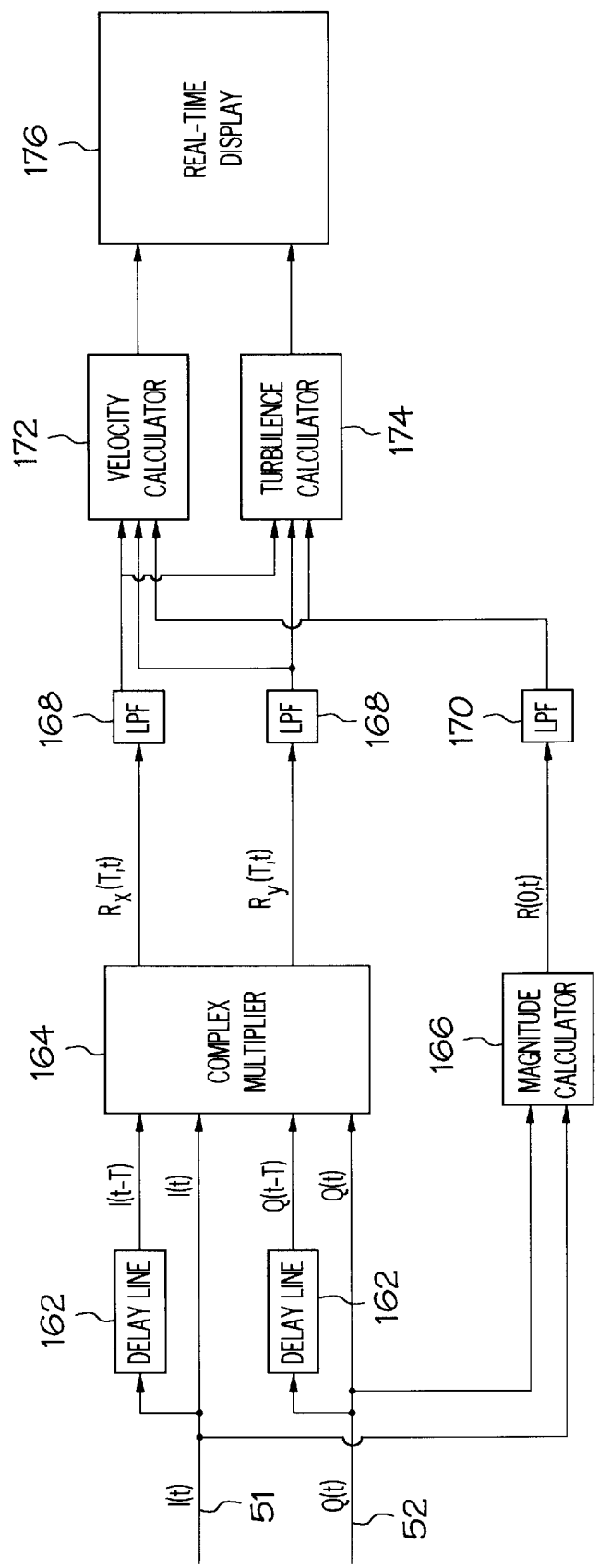
FIG. 13 is a schematic flow diagram illustrating another alternate process and system of the present invention.
Figure 14:
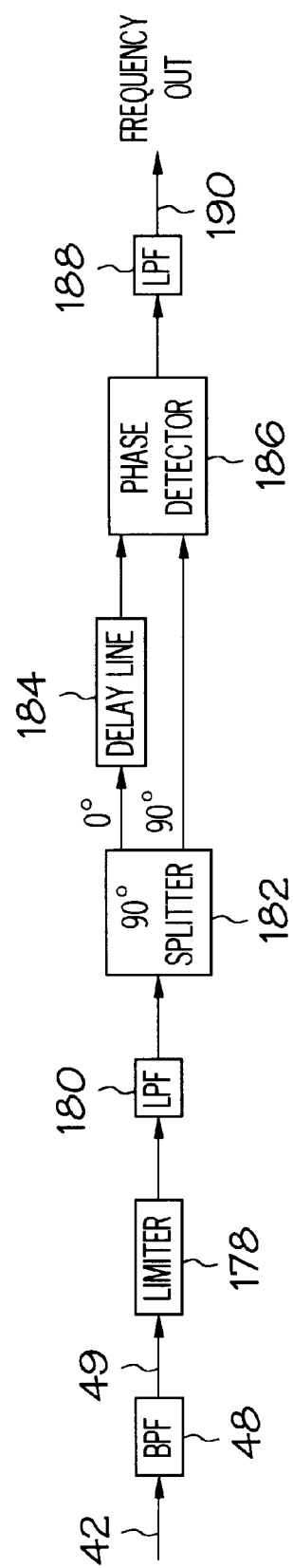
FIG. 14 is a schematic flow diagram illustrating another alternate process and system of the present invention.

We describe two separate specific implementations of velocity and turbulence estimation using the auto-correlation method. The first method utilizes the complex demodulated detector output to obtain both the centroid velocity and an estimate of the power spectrum variance, and is illustrated in FIG. 13. The second method uses a much simpler version of the hardware to obtain an estimate of the central velocity only, and is illustrated in FIG. 14.

As shown in FIG. 13, the first implementation, begins with the complex demodulated output of the CDOCT detector output of FIG. 1. Each of the in-phase I(t) 51 and quadrature Q(t) 52 components of the demodulated output are split into two signal paths, one of which is input into a temporal delay line 162 which delays that signal component by a lag time T. The four signals I(t), I(t−T), Q(t), and Q(t−T) are then input into a complex multiplier circuit 164 which calculates the real $R_x(T,t)$ and imaginary $R_y(T,t)$ components of the complex auto-correlation of I(t) and Q(t):

$$R_x(T,t) = Re[[I(t)+jQ(t)][I(t-T)+jQ(t-T)]],$$ Equation 23

$$R_y(T,t) = Im[[I(t)+jQ(t)][I(t-T)+jQ(t-T)]],$$ Equation 24

A separate magnitude circuit or algorithm 166 is used to calculate the magnitude of the demodulated detector output:

$$R(0, t) = \sqrt{I(t)^2 + Q(t)^2}$$ Equation 25

The real and imaginary components are separately low-pass-filtered, as desired, as shown in block 168, in order to average the resulting estimate of the zero-lag element of the auto-correlation function. The magnitude R(0,t) is also low-pass filtered as shown in block 170. All three signals are then used as the input variables into velocity and turbulence calculators 172, 174, which perform these calculations using equations 21 and 22 and the relations:

$$\phi(T, t) = \tan^{-1}\frac{R_y(T, t)}{R_x(T, t)},$$ Equation 26

$$|R(T, t)| = \sqrt{R_x(T, t)^2 + R_y(T, t)^2}.$$ Equation 27

The resulting estimates of the central velocity and turbulence are then digitized in A/D converters and prepared for combination with the magnitude-only OCT image and display 176. Several display types may be implemented. In one, the velocity estimate is thresholded and saturated according to the user preferences or a pre-established algorithm as before, color coded according to one of the color schemes previously discussed, and overlayed onto the magnitude image. In this case, the turbulence estimate may be treated in the same manner in that it would be thresholded and saturated according to user-specified limits, overlayed onto the corresponding magnitude-only OCT image, and displayed on a separate monitor from the velocity image.

A second implementation which combines velocity and turbulence estimates along with the magnitude-only OCT, image all into one display proceeds as follows. In this case, the velocity data is first thresholded and saturated according to user-specified limits as before. The velocity data is color-coded into two colors representing positive and negative flow, for example blue and red, respectively. In the next step, in those regions in which the velocity data is within the pre-set saturation and threshold limits, the turbulence data is used to change the hue of the velocity color by adding some additional coloring in an amount which is proportional to the amount of turbulence estimated. For positive and negative velocities represented by blue and red, the turbulence may be represented by adding the hue of green, so that positive flow plus maximum turbulence approaches the color cyan, and negative flow plus maximum turbulence approaches the color yellow.

It is to be understood that the calculations illustrated in FIG. 13 may be performed using circuits or integrated circuits designed specifically for this purpose, or alternatively the demodulated detector output may be directly digitized using A/D converters and the bulk of the calculations may be performed digitally in a computer.

Now referring to FIG. 14, in a second implementation of velocity and turbulence estimation, the velocity estimate can be extracted directly from the detector signal with a simple hardware implementation of the auto-correlation method. As described earlier, the centroid velocity estimate corresponds to the zero-lag element of the signal auto-correlation. As described with respect to FIG. 1, interferometric component of the OCT signal (interferogram) can be isolated by band pass filtering the photodetector output. Rewriting Equation 1:

$$i_D(t) \cdot \cos(2\pi(f_r - f_s)t + \alpha(t)), \quad \text{Equation 28}$$

where A(t) is the envelope of the interferogram, $f_r$ is the Doppler shift frequency of the interferogram due to the reference arm scanning, $f_s$ is the Doppler shift frequency due to movement in the sample, and $\alpha(t)$ is an arbitrary, time varying phase term. A high dynamic range limiter 178 (such as the AD606 Demodulating Logarithmic Amplifier with Limiter output from Analog Devices, Inc) eliminates the amplitude variation in the signal, preserving only frequency information. A low pass filter 180 passes only the fundamental sinusoidal frequency component of the signal, which can now be written as:

$$A \cdot \cos(2\pi(f_r - f_s)t + \alpha(t)), \quad \text{Equation 29}$$

where A is now a constant amplitude. A 90° power splitter 182 (such as the model PSCQ-2 series from Mini-Circuits, Inc.) divides the signal into two paths, with one path phase shifted by 90°, and becomes $$A \cdot \cos(2\pi(f_r - f_s)t + \alpha(t) - 90°). \quad \text{Equation 30}$$

The signal in the 0° path is delayed by a fixed time T by a delay line 184 (such as the 2214 series Delay Lines from Data Delay Devices, Inc.) and becomes $$A \cdot \cos(2\pi(f_r - f_s)(t - T) + \alpha(t - T)) \quad \text{Equation 31}$$

The signals in the two paths are then input to a phase detector 186. A phase detector is a device which takes as its input two signals with the same frequency, and which gives an output proportional to the product of the amplitudes of the input signals, and to the phase difference between the input signals. An example of a phase detector is the ZRPD-1 from Mini-Circuits, Inc., which gives an output proportional to the cosine of the phase difference between the input signals.

Using such a phase detector 186, and a 90° splitter 182 with the 90° phase shift in the undelayed path, the output of the phase detector and low pass filter 188 is:

$$\frac{A^2}{2} \cdot \sin(2\pi(f_r - f_s)T + \alpha(t) - \alpha(t - T)). \quad \text{Equation 32}$$

Assuming that the phase term φ(t) does not change significantly over the time period T, equation 32 becomes $$\frac{A^2}{2} \cdot \sin(2\pi(f_r - f_s)T). \quad \text{Equation 33}$$

Therefore, the Doppler shift frequency due to flow in the sample, $f_s$, is proportional to the arcsine of the low pass filtered output of the phase detector, offset by the reference arm Doppler shift frequency:

$$f_s = f_r - \frac{\arcsin(2S/A^2)}{2\pi T}, \quad \text{Equation 34}$$

where S is the low pass filtered output of the phase detector 186. Since the center frequency of the interferogram corresponds to the velocity of the sample, according to equation 5, the output 190 of this network represents sample velocity. As described in detail above, this velocity output 190 may be used to generate a colorized velocity image for the sample.

Having described the invention in detail and by reference to the drawings, it will be apparent that modification and variations will be possible without departing from the scope of the invention as defined in the following claims.

What is claimed is:

1. A method for generating a velocity-indicating, tomographic image of a sample in an optical coherence tomography system, the optical coherence tomography system including an interferometer having a reference arm and a sample arm, the method comprising the steps of:

acquiring cross-correlation data from the interferometer;

generating a grayscale image from the cross-correlation data indicative of depth-dependent positions of scatterers in the sample;

processing the cross-correlation data to produce a velocity value and a location of a moving scatterer in the sample;

assigning a color to the velocity value;

merging the color into the grayscale image, at a point in the grayscale image indicative of the moving scatterer's location, to produce a velocity-indicating, tomographic image.

2. The method of claim 1, wherein:

the processing step includes the step of coherently demodulating the cross-correlation data at a Doppler shift frequency of the reference arm; and the assigning step includes the steps of assigning one color for a positive velocity value and assigning another color for a negative velocity value.

3. The method of claim 1, wherein:

the assigning step includes the step of setting the brightness, shade, density or intensity of the color according to a magnitude of the velocity value.

4. The method of claim 1, wherein the processing step includes the step of performing a time-frequency analysis step on the cross-correlation data to extract spectral information from the cross-correlation data as a function of depth.

5. The method of claim 4, wherein the time-frequency analysis step includes the step of performing a short-time Fourier transform on the cross-correlation data.

6. The method of claim 5, wherein:

the time-frequency analysis step is performed upon a plurality of time-windows of the cross-correlation data to produce a corresponding plurality of depth-dependent power spectrum values;

the processing step further includes the step of calculating depth-dependent velocity values for each of the power spectrum values; and the assigning step is performed for each of the plurality of depth-dependent velocity values.

7. The method of claim 6, wherein the calculating step includes the step of calculating a centroid, indicative of an estimate of mean scatter velocity, for each of the power spectrum values.

8. The method of claim 6, wherein the plurality of time-windows overlap one another.

9. The method of claim 4, wherein:

the time-frequency analysis step includes the step of introducing the cross-correlation data through a plurality of band-pass filters, one portion of the plurality of band-pass filters passing frequencies below a Doppler shift frequency of the reference arm and another portion of the plurality of band-pass filters passing frequencies above the Doppler shift frequency of the reference arm, the output of the plurality of band-pass filters representing a depth-dependent power spectrum; and the processing step includes the step of calculating a centroid from the power spectrum, indicative of an estimate of mean scatter velocity, the estimate being the velocity value.

10. The method of claim 4, wherein:

the method further comprises the step of coherently demodulating the cross-correlation data at the Doppler shift frequency of the reference arm;

the time-frequency analysis step includes the step of introducing the demodulated cross-correlation data through a plurality of complex band-pass filters, one portion of the plurality of complex band-pass filters passing frequencies below a Doppler shift frequency of the reference arm and another portion of the plurality of complex band-pass filters passing frequencies above the Doppler shift frequency of the reference arm, the output of the plurality of complex band-pass filters representing a depth-dependent power spectrum;

the processing step includes the step of calculating a centroid from the power spectrum, indicative of an estimate of mean scatter velocity, the estimate being the velocity value; and the assigning step includes the steps of assigning one color for a positive velocity value and assigning another color for a negative velocity value.

11. The method of claim 4, wherein:

the method further comprises the step of coherently demodulating the cross-correlation data at the Doppler shift frequency of the reference arm, to generate in-phase cross-correlation data and quadrature cross-correlation data;

the time-frequency analysis step includes the steps of introducing the in-phase cross-correlation data through a first plurality of band-pass filters, one portion of the first plurality of band-pass filters passing frequencies below a Doppler shift frequency of the reference arm and another portion of the first plurality of band-pass filters passing frequencies above the Doppler shift frequency of the reference arm, introducing the quadrature cross-correlation data through a second plurality of band-pass filters, one portion of the second plurality of band-pass filters passing frequencies below a Doppler shift frequency of the reference arm and another portion of the second plurality of band-pass filters passing frequencies above the Doppler shift frequency of the reference arm, squaring the output of each of the first and second pluralities of band-pass filters, summing the squares, and taking a square root of the sum to produce a depth-dependent power spectrum;

the processing step includes the step of calculating a centroid from the power spectrum, indicative of an estimate of mean scatter velocity, the estimate being the velocity value; and the assigning step includes the steps of assigning one color for a positive velocity value and assigning another color for a negative velocity value.

12. The method of claim 1, wherein:

the acquiring and processing steps are repeated a plurality of times for a lateral position of the sample arm;

the method includes the step of averaging the velocity values produced in the processing steps to generate an average velocity value; and the assigning step includes the step of assigning a color to the average velocity value.

13. The method of claim 1, wherein:

the acquiring step includes the step of repeatedly acquiring cross-correlation data at a predetermined depth, producing a plurality of cross-correlation data readings at the predetermined depth; and the processing step includes the step of performing a time frequency analysis on the plurality of cross-correlation readings to obtain a velocity estimate at the predetermined depth.

14. An optical coherence tomography system comprising:

an interferometer including an optical radiation source, a sample arm and a reference arm, the interferometer generating a cross-correlation data output of a sample in the sample arm; and a data processing system, operatively coupled to the interferometer, processing the cross-correlation data to generate a grayscale image from the cross-correlation data indicative of depth dependent positions of scatterers in the sample, processing the cross-correlation data to produce a velocity value and a location of a moving scatterer in the sample, assigning a color to the velocity value, and merging the color into the grayscale image at a point in the grayscale image indicative of the moving scatterer's location.

15. The optical coherence tomography system of claim 14, wherein the data processing system includes:

a demodulation device, operatively coupled to the output of the interferometer;

a Fourier transform device, operatively coupled to the output of the demodulation device; and a velocity estimation device operatively coupled to the output of the Fourier transform device.

16. The optical coherence tomography system of claim 14, wherein the data processing system includes:

a plurality of band-pass filters, operatively coupled to the output of the interferometer, one portion of the plurality of band-pass filters passing frequencies below a Doppler shift frequency of the reference arm and another portion of the plurality of band-pass filters passing frequencies above the Doppler shift frequency of the reference arm; and a velocity estimation device operatively coupled to the output of the plurality of band-pass filters.

17. The optical coherence tomography system of claim 14, wherein the data processing system includes:

a demodulation device, operatively coupled to the output of the interferometer;

a plurality of complex band-pass filters, operatively coupled to the output of the demodulation device, one portion of the plurality of complex band-pass filters passing frequencies below a Doppler shift frequency of the reference arm and another portion of the plurality of complex band-pass filters passing frequencies above the Doppler shift frequency of the reference arm; and a velocity estimation device operatively coupled to the output of the plurality of band-pass filters.

18. The optical coherence tomography system of claim 14, wherein the data processing system includes:

a demodulation device, operatively coupled to the output of the interferometer, having an in-phase data output and a quadrature data output;

a first plurality of band-pass filters, operatively coupled to the in-phase data output of the demodulation device, one portion of the first plurality of band-pass filters passing frequencies below a Doppler shift frequency of the reference arm and another portion of the first plurality of band-pass filters passing frequencies above the Doppler shift frequency of the reference arm;

a second plurality of band-pass filters, operatively coupled to the quadrature data output of the demodulation device, one portion of the second plurality of band-pass filters passing frequencies below a Doppler shift frequency of the reference arm and another portion of the second plurality of band-pass filters passing frequencies above the Doppler shift frequency of the reference arm; and a velocity estimation device operatively coupled to the output of the first and second pluralities of band-pass filters.

19. An optical coherence tomography system comprising:

an electromagnetic radiation source generating source radiation;

a reference optical reflector;

means for directing the source radiation to a sample;

means for directing the source radiation to the reference reflector;

means for combining reflected radiation from the sample and from the reference reflector, to produce combined reflected radiation;

means for generating a grayscale image from the combined reflected data indicative of depth dependent positions of scatterers in the sample;

means for processing the combined reflected data to produce a velocity value and a location of a moving scatterer in the sample;

means for assigning a color for the velocity value; and means for merging the color into the grayscale image at a point in the grayscale image indicative of the moving scatterer's location.

20. The optical coherence tomography system of claim 19, wherein the assigning means includes means for assigning a first color for a positive velocity value and means for assigning a second color for a negative velocity value.

21. The optical coherence tomography system of claim 19, wherein the assigning means includes means for assigning a brightness, shade, density or intensity of the color according to a magnitude of the velocity value.

* * * * *